(12) United States Patent
Ruse et al.

(10) Patent No.: US 12,427,305 B2
(45) Date of Patent: Sep. 30, 2025

(54) METHOD AND APPARATUS USING A PHASED ARRAY AMPLIFIER SYSTEM TO TREAT BONE OR TISSUE INFECTIONS

(71) Applicant: MedAmp Electronics LLC, Franklin, NC (US)

(72) Inventors: Richard B. Ruse, Sandy Springs, GA (US); E. David Crawford, Denver, CO (US); William L. Nabors, Marietta, GA (US); Sean Brugman, Lakewood, CO (US); Scott J. Bohanan, Statesboro, GA (US); Paul Arangua, Lakewood, CO (US)

(73) Assignee: MedAmp Electronics LLC, Franklin, NC (US)

( * ) Notice: Subject to any disclaimer, the term of this patent is extended or adjusted under 35 U.S.C. 154(b) by 0 days.

(21) Appl. No.: 17/878,608

(22) Filed: Aug. 1, 2022

(65) Prior Publication Data

US 2023/0031498 A1    Feb. 2, 2023

Related U.S. Application Data

(60) Provisional application No. 63/227,687, filed on Jul. 30, 2021.

(51) Int. Cl.
*A61N 1/20* (2006.01)
*A61N 1/02* (2006.01)
*A61N 1/05* (2006.01)
*A61N 1/08* (2006.01)

(52) U.S. Cl.
CPC .............. *A61N 1/205* (2013.01); *A61N 1/025* (2013.01); *A61N 1/0502* (2013.01); *A61N 1/08* (2013.01)

(58) Field of Classification Search
None
See application file for complete search history.

(56) References Cited

U.S. PATENT DOCUMENTS

| | | |
|---|---|---|
| 5,913,856 A | 6/1999 | Chia et al. |
| 6,106,524 A | 8/2000 | Eggers et al. |
| 8,216,219 B2 | 7/2012 | Desinger et al. |
| 8,706,258 B2 | 4/2014 | Nabors, Sr. et al. |
| 8,965,527 B2 | 2/2015 | Ruse et al. |
| 9,486,625 B2 | 11/2016 | Crawford et al. |

(Continued)

FOREIGN PATENT DOCUMENTS

WO    2020097162 A1    5/2020

*Primary Examiner* — Michael W Kahelin
(74) *Attorney, Agent, or Firm* — William H. Dippert; Laurence A. Greenberg; Werner H. Stemer

(57) ABSTRACT

A method and apparatus for treating bone or other infection in a patient to minimize the number of limb amputations which employs a unique, three-dimensional software-controlled electronic phased array amplifier system using arbitrary waveforms that dynamically and proportionally steer electrical currents by using two or more current vector paths, sequentially or simultaneously, through a defined infected area containing electrically-conductive ionic solutions so as to obtain 100% treatment using low or high voltage, low current that delivers electrical stimulation (ES) using a low DC current through and or around the defined infection treatment area. The minimally invasive treatment of the infection requires no radiation or chemotherapy that could be harmful to the patient.

11 Claims, 16 Drawing Sheets

(56) References Cited

U.S. PATENT DOCUMENTS

| | | |
|---|---|---|
| 9,592,160 B2 | 3/2017 | Bacon et al. |
| 9,616,142 B2 | 4/2017 | Ehrensberger et al. |
| 10,278,761 B2 * | 5/2019 | Long .................... A61B 18/12 |
| 10,596,384 B2 | 3/2020 | Gellman et al. |
| 10,638,931 B2 | 5/2020 | Peterson |
| 10,881,298 B2 | 1/2021 | Peterson |
| 2002/0111615 A1 | 8/2002 | Cosman et al. |
| 2003/0069573 A1 | 4/2003 | Kadhiresan et al. |
| 2003/0195503 A1 | 10/2003 | Jain et al. |
| 2004/0267340 A1 | 12/2004 | Cioanta et al. |
| 2005/0165390 A1 | 7/2005 | Mauti et al. |
| 2007/0242743 A1 * | 10/2007 | Scherman ............... H03F 3/085 |
| | | 375/238 |
| 2007/0255269 A1 | 11/2007 | Shin |
| 2014/0052216 A1 * | 2/2014 | Long .................. A61B 18/1477 |
| | | 607/50 |
| 2015/0196351 A1 * | 7/2015 | Stone ...................... A61N 1/28 |
| | | 606/41 |
| 2019/0247234 A1 * | 8/2019 | Prakash ............ A61F 13/00068 |
| 2020/0147245 A1 | 5/2020 | Hobble et al. |
| 2021/0059554 A1 * | 3/2021 | Armbruster ............ A61B 17/64 |
| 2021/0401288 A1 * | 12/2021 | Weil .................... A61B 5/0064 |

* cited by examiner

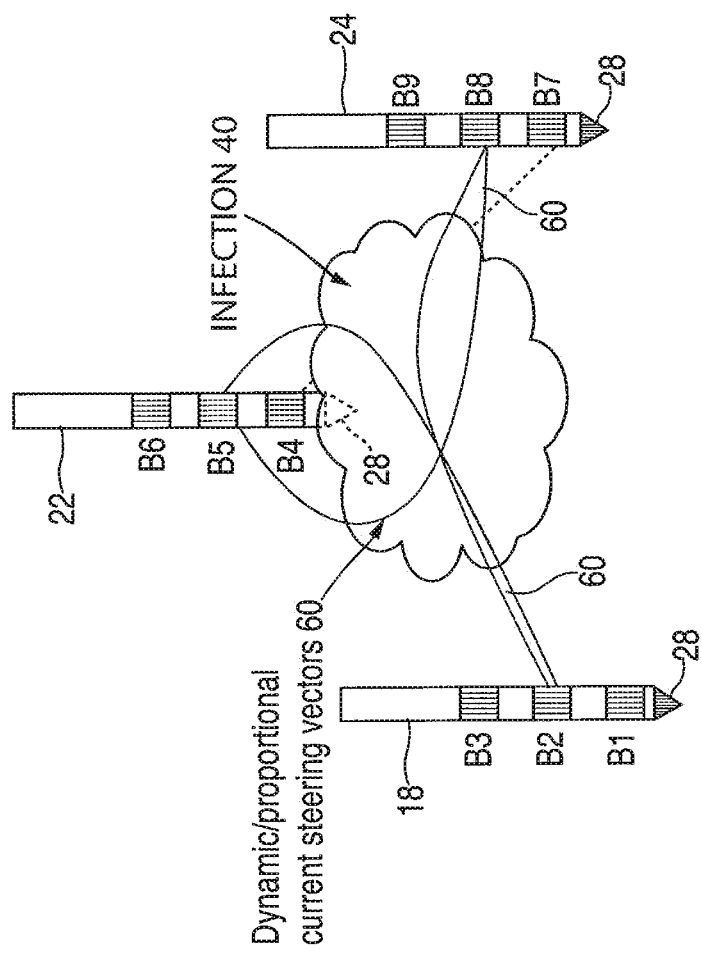

DC VECTOR ROTATION PHASED ARRAY
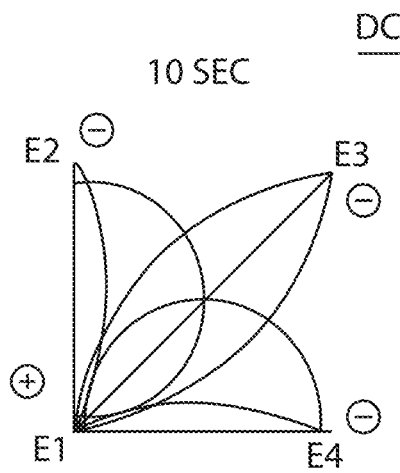
FIG.9B(i)
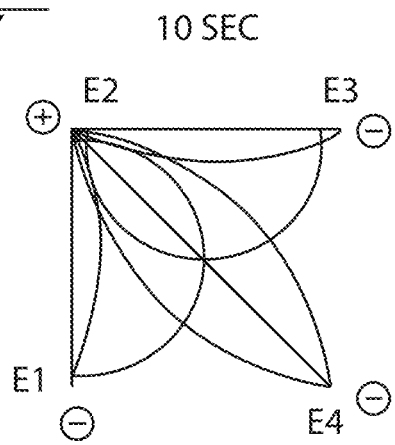
FIG.9B(ii)
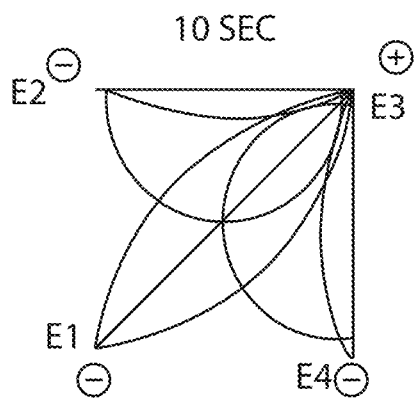
FIG.9B(iii)
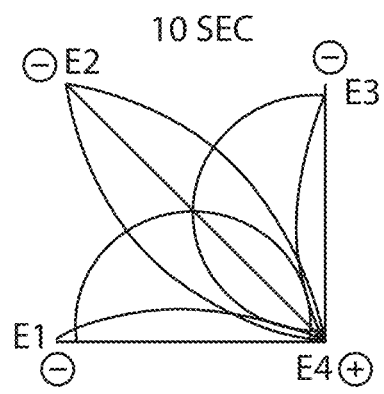
FIG.9B(iv)
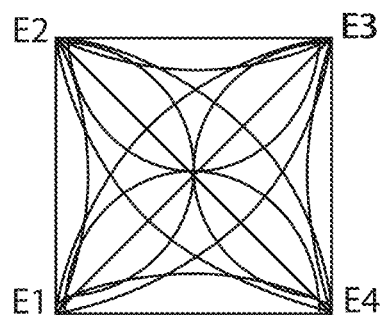
(100% COVERAGE)
LOW DC VOLTAGE
STEADY STATE
FIG.9B(v)
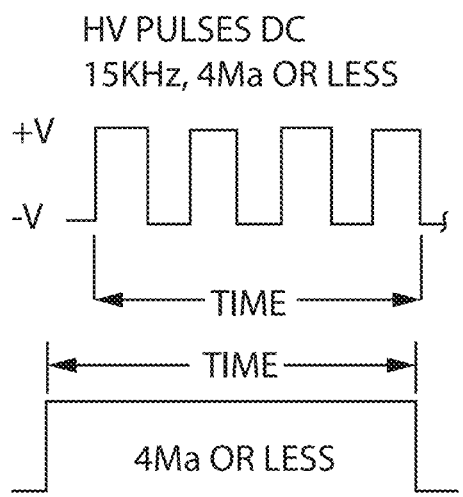
HV PULSES DC
15KHz, 4Ma OR LESS
FIG.9B(vii)

METHOD AND APPARATUS USING A PHASED ARRAY AMPLIFIER SYSTEM TO TREAT BONE OR TISSUE INFECTIONS

CROSS-REFERENCE TO RELATED PATENT APPLICATION

This patent application is based upon and claims the priority of U.S. Provisional Patent Application Ser. No. 63/227,687, filed Jul. 30, 2021, incorporated herein by reference in its entirety.

FIELD OF THE INVENTION

This invention is directed to the treatment of bone or tissue infections in a patient resulting from fractures or injury, hip or knee implants, or any disease that causes infections whereby the antibiotic and surgery therapies have not been able to treat or eliminate the infection. More particularly, this invention is directed to the treatment of bone or tissue infection in a patient which comprises dynamically and proportionally steering electrical current vectors to a predetermined defined area to resistively and/or electrically stimulate the defined area and eradicate the bacterial bio-films, bacteria, viruses, or fungus causing infections. Potential treatments include, but are not limited to, the treatment of infections in bones or joints, the treatment of infections in bone or joint fractures, the treatment of infections in implants such as hip and knee implants, the treatment of infections resulting from impact injuries such as leg fractures, diabetes or other diseases, and the treatment of bed sores or other dermal, subdermal or deep tissue infections and conditions.

BACKGROUND OF THE INVENTION

Bone or tissue infections are more prevalent than most people realize. Predisposing factors include indwelling catheters; infections of the skin, throat, ears, lung, heart, and genital-urinary tract; penetrating or nonpenetrating trauma; joint implants, and underlying diseases or conditions such as diabetes, renal failure, hemoglobinopathies, and immunosuppression. More often than not, the host is healthy and the source of the bacteria is obscure, with the initiating bacteria possibly a complication from an impact injury, joint implant infection, surgery wherein knee or hip implants are successfully installed; however, bacteria enters through unseen processes and may evolve into a serious or life threatening septic, systemic type infection.

Known methods to treat infections in bone or tissue mostly involve surgical intervention and extensive courses of IV and or oral antibiotics. If these treatments are ineffective within a given time period (likely three to six weeks), then the surgeon is left with only one option to save the patient's life: amputation. Therefore, there is a definite need for a more effective treatment of infections in bone or tissue and artificial knee, hip implants and accident or injury fractures or similar.

OBJECTS OF THE INVENTION

It is an object of the invention to provide a method and apparatus for treating bone or tissue infection caused by bacteria, viruses, or fungus.

It is also an object of the invention to provide a method and apparatus for treating bone or tissue infections that are highly resistant to antibiotic therapy.

It is also an object of the invention to provide a method and apparatus for treating bone infections within the bone or adjacent to the bone (focal therapy).

It is also an object of the invention to employ several electrical therapies, depending on the type of infection, to work in concert with antibiotic therapy to quickly kill bacterial bio-membranes, bacterial, viral, or fungal infections. Direct current (DC) is used to treat bone and/or tissue infections using heat/hyperthermia and/or electrical stimulation (ES) using low DC current on the order of microamps to milliamps at low or high voltage to disrupt the bio-membranes that encase bacterial colonies or to destroy any virus or fungus.

It is a further object of the invention to provide a method and apparatus for treating bone or tissue infections that may have been untreatable using existing methods such as antibiotics and surgical therapies.

It is a yet further object of the invention to provide a method for treating bone or tissue infection that comprises surrounding the infected area with at least three electrode shafts and applying sufficient DC electrical voltage and current in dynamically and proportionally steered current vectors to destroy bacterial, viral, and fungal infections.

It is a yet further object of the invention to provide an apparatus comprising at least three, preferably four or six electrode shafts, each electrode shaft having one or more electrode bands or contact points and being capable of applying sufficient electrical voltage and current in dynamically and proportionally steered current vectors to destroy infection or infections.

It is a yet further object of the invention to provide a method and apparatus for treating bone or tissue infection wherein the electrical current applied has waveforms that are chosen by proprietary software to be particularly effective.

It is a further object of the invention to provide a method and apparatus for treating bone or tissue infection where each electrode shaft comprising electrodes has a distal sharp tip comprising a rigid dissolvable salt coating or compound or a functional equivalent, to eliminate tissue damage within a patient after the electrode shaft is inserted.

It is a yet further object of the invention to provide a method and apparatus wherein each electrode band or contact point on a shaft comprises a current and thermal sensor.

It is a yet further object of the invention to provide a method of treating a bacterial, viral, or fungal infection within a patient's body, in bone and or tissues, which comprises dynamically and proportionally steering preferentially DC current vectors to a predetermined defined area comprising the infection to electrically treat the defined area to irradicate the infection.

It is a yet further object of the invention to provide a phased array amplifier system for treating an infection within a patient's body, which system comprises:
  three or more electrode shafts that define an area;
  a microprocessor or Field Programmable Gate Array (FPGA) for generating instructive signals; and
  three or more phased array amplifiers for receiving instructive signals from the microprocessor or FPGA and generating signals to the electrode bands,
  wherein voltages of the electrodes are varied to dynamically and proportionally steer current vectors to and through the defined area to electrically destroy or kill the biological membrane of the infection to reduce or eliminate the infection while sparing the host tissues.

It is a yet further object of the invention to provide an amplifier system which is suitable for treating an infection which occurs in the prostate, breast, liver, lungs, pancreas, kidneys, uterus, skin, ovaries, muscle, tissue, or bone.

It is a yet further object of the invention to provide a system for treating an infection within a patient's body, which comprises:
- three or more electrode shafts that define an area comprising the infection, each electrode shaft having at least one electrode band positioned along the shaft;
- a microprocessor or FPGA configured to generate instructive signals that are DC voltage and current or arbitrary waveforms from about 15 KHz to about 25 KHz; and
- a phased array amplifier system configured to receive instructive signals from the microprocessor or FPGA and to deliver signals to the electrodes and/or electrode bands,
- wherein the microprocessor or FPGA is configured to control the phased array amplifiers to proportionately vary the voltage amplitude of signals to the electrode bands to dynamically steer and focus ionic current vectors to create and steer an electrical DC voltage and current anywhere in three dimensions within the defined area between the electrode shafts to resistively treat or use ES to draw ionic current through the defined area to eliminate bacterial infections or reduce bacterial load.

It is a yet further object of the invention to provide a system for treating infection within a patient's body which comprises:
- three or more electrode shafts that define an area comprising a bacterial, viral, or fungal infection, each electrode shaft having at least one electrode band positioned along the shaft; and
- a computer microprocessor- or FPGA-controlled electronic amplifier array which is configured to deliver signals that are DC arbitrary steady state or pulsed waveforms of from about 15 KHz to about 25 KHz to the electrode bands,
- wherein the computer-controlled microprocessor or FPGA is configured to control the phased array amplifiers to proportionately vary the DC voltage amplitude of signals to the electrode bands to dynamically steer and focus ionic current vectors, which are regulated and current limited to a maximum value of 4 mA to create and steer treatment zone anywhere in three dimensions within the area between the three or more electrode shafts, and
- wherein the defined area is treated with a low current therapy on the order of about 10 µA, microamps to about 4 mA, (milliamps) DC that sufficiently reduces or eliminates the infection while minimizing damage to surrounding healthy host tissue.

In yet another object of the invention, a joint, such as a hip, knee, or fractures thereof, a hip or knee implant, or a bone, tissue or a fracture thereof could be treated to eliminate or prevent infection. The voltage and current should be in the range of a few millivolts to about 12 volts and very small chronic electrical currents of microamps to about 4 mA. Particularly in the use of DC voltage and current the bio-membranes that protect bacterial colonies are vulnerable to destruction using very small DC electrical currents between about 10 µA to about 4 mA. Platinum plating is the preferred metallic plating metal due to its absolute inert reaction to electrolysis or corrosion from applied electrical currents in human body chemically.

It is a yet further object of the invention to provide a method for treating bacterial, viral, or fungal infection within a patient's body, which comprises:
- positioning three or more electrode shafts that define an area comprising an infection, each electrode shaft having at least one electrode band positioned along the shaft;
- generating instructive signals from a microprocessor or FPGA whereby computer processor-controlled phased array amplifiers are configured to deliver signals that are DC arbitrary steady state or pulsed waveforms of a frequency of from about 15 KHz to about 25 KHz; and
- receiving the instructive signals from the microprocessor or FPGA in an amplifier array configured to receive such signals and to deliver signals to the electrode bands,
- wherein the microprocessor or FPGA is configured to control the phased array amplifiers to proportionately vary the voltage amplitude of signals to the electrode bands to dynamically steer and focus ionic current vectors to create and steer a treatment zone anywhere in three dimensions within the defined area between the electrode shafts to electrically treat the defined area to reduce or eliminate the infection using a DC voltage and current.

It is a yet further object of the invention to provide a system for treating bacterial, viral, or fungal infection internal or external to a patient's body, which comprises:
- a microprocessor or FPGA configured to generate instructive signals that are DC arbitrary waveforms of a frequency of from about 15 KHz to about 25 KHz;
- three or more electrode shafts that define an area comprising the infection, each electrode shaft having at least one electrode band positioned along the shaft; and
- an amplifier array configured to receive instructive signals from the micro-processor or FPGA and to deliver signals to the electrode bands,
- wherein the microprocessor or FPGA is configured to control the phased array amplifiers to proportionately vary the voltage amplitude of signals to the electrode bands to dynamically and proportionally steer and focus ionic current vectors to create and steer a treatment zone anywhere in three dimensions within the defined area between the electrodes in concert with three or more subcutaneous electrodes to electrically treat the defined area using a DC voltage and current to reduce or eliminate the infection.

It is a yet further object of the invention to provide a method of treating bacterial, viral, or fungal infection within a patient's body, which comprises:
- positioning three or more electrode shafts in or around an infected area in or on a patient to create a defined area, where each electrode shaft has at least one electrode band;
- delivering signals that are DC arbitrary waveforms or of a frequency of between about 15 KHz; and 25 KHz electrode bands; and
- proportionately varying voltage amplitude and pulse-widths between the three or more electrode shafts to dynamically steer and focus ionic current vectors to the defined area to create and steer a treatment zone or ES in three dimensions within the defined area to electrically treat the defined area of bacteria, viruses, or fungi or bio-membrane to reduce or eliminate the infection.

These and other objects of the invention will become more apparent from the description below taken in conjunction with the attached detailed drawings.

SUMMARY OF THE INVENTION

This invention is directed to the treatment of bone or tissue infections resulting from three main areas of medically unmet needs. Bone or tissue infections may occur anywhere in the human body; however, the focus of this invention is to successfully treat leg impact injuries/fractures, hip and knee implant infections which can lead to excessive and life-threatening infections, sepsis and/or conditions if the infections are not treated promptly and properly. Another goal is to minimize the number of amputations resulting from three main sources, that is, leg, knee, or hip fractures or breaks, knee, or hip implants, and diabetic infections in leg and feet areas where blood flow is compromised and antibiotics alone cannot kill the unwanted bacterial bio-membranes, bacterial, viral, or fungal infections.

Applying an electrical direct current (DC) through an ionic mass or ionic solution produces electrolysis and breaks down the components of $H_2O$ creating one electrode that produces oxygen and one that produces hydrogen. In addition, with a sodium (ionic) solution, chlorine and/or hydrogen peroxide may be produced through the process of electrolysis. Also, applying an electrical alternating current (AC) through an ionic mass or liquid solution produces heating or hyperthermia. The only difference between DC and AC currents applied through an ionic mass is that with DC current one electrode is an anode and the other electrode is a cathode for enough time that a DC electrolysis function can be established to kill bio-membranes and bacteria. Chemical reactions occur at the two electrodes that take electron voltage, and current applied to the electrodes, and the first electrode in the ionic mass converts the energy into ionic current through the mass or solution. At the second electrode, the ionic current is converted back into electron current of the opposite polarity. Electron current can be conducted through a metal conductor such as a wire where ionic current cannot flow through a wire, only an ionic solution or ionic mass. When AC current is used, each of two electrodes where an AC voltage and current are applied causes each electrode to convert the electron current flow into an ionic current flow. However, when AC current is applied through an ionic media, each electrode becomes an anode and a cathode by changing functions, alternating back and forth at the frequency of the AC current. Thus, AC or DC current will produce heating through an ionic mass provided that an ionic solution exists in sufficient density for an ionic current to flow and generate heat. DC currents are advantageous because current flows in one direction only and can induce an electrolysis effect whereby chlorine and hydrogen peroxide may work in concert with antibiotic therapy to destroy infections and several university studies have demonstrated that DC voltage and low current do effectively kill bio-membranes and bacteria that cause bone and tissue infections. The studies have revealed that DC voltage and low current destroy the bio-membranes and bacterial colonies that cannot be treated entirely by using antibiotics and the ever increasing bio-resistance to antibiotics meaning that there is an evolutionary treatment of antibiotics that are becoming resistant to certain bacteria whereby they fail to treat the targeted infections and bacterial loads or concentrations that cure an infection within a patient.

According to an aspect of the invention, a method and apparatus are provided for dynamically and proportionately steering or selecting two or more current vector paths, sequentially or simultaneously, for treating and destroying infections within a bone or joint such as a hip or knee or in other internal or adjacent tissues. Other traditional devices use a single current path or devices that deliver current across one or more current vector pathways. However, they cannot dynamically and proportionally steer current to induce a three-dimensional treatment area that can destroy bacteria 100% within a known infected area by altering the voltage, current amplitude, and pulse-widths, or employ arbitrary waveforms through each pathway in three dimensions, that being the X, Y, and Z planes, within a targeted treatment area.

According to another aspect of the invention, an electrode system comprises three or more essentially non-conductive longitudinally extending members or shafts that will each comprise one or more electrode bands or contact points. Each electrode band or contact point is in electrical communication with any amplifier within the array, and current and thermal sensors are attached to each electrode band or contact point. Each current and thermal sensor is in electrical communication with a controller or microprocessor or FPGA. These shafts are positioned strategically around and in close proximity to an infection area to be treated.

According to another aspect of the invention, a method and apparatus use shafts with specifically designed electrodes that are electrically and mechanically manufactured to optimize the treatment for the specific bone or tissue infection to be treated. Another method to destroy bacteria, viruses, or fungus uses steady state DC low voltage or pulsed DC at higher voltages and low current that will rupture the biological membrane of the infection(s), which causes destruction of the bio-membrane and allows the bacteria within that structure of the infection to be destroyed while sparing the host tissue and bone that are treated.

According to another aspect of the invention, electronic circuitry waveforms are employed which include, but are not limited to, arbitrary waveforms of any form, amplitude, or pulse-width (sine, square, triangle, curved, positive, or negative, with varying pulse width modulation) using direct current (DC) and frequencies of voltage dependent upon the situation/mass and the treatment required. The waveform shapes are generated by a processor under software control interfaced with a computer. The energy is further amplified and delivered differentially between amplifiers without the use of a ground patch or ground return pathway.

According to another aspect of the invention, the electrodes electrically treat the infection within or around bone (e.g., a leg, hip, or knee) or in internal infected tissue or deep tissue where antibiotics have failed to treat a bacterial infection. The electrodes are positioned around, or may enter, the bone or tissue itself for the purpose of destroying the bacteria, viruses, or fungus. A knee or hip implant component may serve as an active electrode whereby the phased array amplifiers treat the bone from an intra-medullary location which may enhance treatment of deep bone infections where antibiotics cannot easily access the infection for treatment. A microprocessor or FPGA will vary the voltage amplitude, current intensity, and pulse-width to treat, deliver ES and maintain thermal and current limit averaging within the bone or tissue infection. The current pulses are kept within the area defined by the shaft placement via dynamic and proportional current steering as commanded via the microprocessor or FPGA so that healthy host tissue is not affected by treating the bone or tissue infection.

According to another aspect of the invention, an amplifier phased array, in conjunction with the microprocessor or FPGA, can focus energy in any area within the bone or tissue infection to insure destruction of all bacteria, viruses or fungus. This is done by proportionally varying the voltage amplitude and pulse-widths between electrodes to dynamically and proportionally shift, steer, or create a "treatment zone" anywhere in the bone or tissue infection in three dimensions.

In another aspect of the invention, a microprocessor or FPGA will start the treatment protocol by slowly ramping the voltage and current via a computer menu up to a level, for example, in the microampere or milliampere range, where the surgeon can verify that all amplifiers are conducting current as specified to achieve the desired DC currents or electrical pulse therapies. The thermal and current sensors provide data for the microprocessor or FPGA so the software commands can direct the phased amplifier array drive voltage amplitudes and pulse-widths while managing all voltage, current and power level therapies to keep them within normal limits for patient safety.

Using an AC voltage and current therapy, a thermal goal may be used if indicated to uniformly heat and elevate the bone or tissue infection area to a temperature of from about 38° C. body temperature to no more than about 48° C. More specifically, the bone infection area is heated to a temperature from about 38° C. to no more than about 48° C., for the purpose of protecting the integrity of the bone, for from about 5 to about 30 minutes to assist the DC voltage and current therapy or until all infection within the bone is destroyed, and the tissue infection area is heated to a temperature from about 38° C. to no more than about 48° C. for from about 5 to about 30 minutes or until all infection within the tissue is destroyed.

The time to heal from this procedure should be from a few days to a week or so, at which point MRI, CT, and/or ultrasound scans can be employed to analyze the area of interest and verify that the infection has been destroyed. In addition to the quick healing time, an advantage to this treatment is that unlimited additional treatments may be made to "touch up" any infection that was missed during the initial treatment. Furthermore, no damaging radiation or chemotherapy would be required to affect a cure.

In another aspect of the invention, a microprocessor or FPGA is used to drive a preamplifier and amplifier which dynamically and proportionally steer current vectors between specially-designed electrodes that are electroplated on the electrode shafts and are preferably plated with platinum since it is unaffected by any electrolysis or deleterious effects between the electrodes and bone or tissue and are inserted strategically around or into the bone using an infinite variety of waveforms which include, but are not limited to, arbitrary waveforms of any shape, amplitude or pulse-width using DC—of voltage, and current of from about 15 KHz to 25 KHz, dependent upon the infection and the treatment required. The surgeon can use the microprocessor or FPGA to vary the voltage amplitude, current intensity, power in Watts and/or pulse-width and select any arbitrary waveform to treat and maintain current averaging throughout the entire targeted infection to a uniform or increasing current sufficient to destroy the offending bacterial, viral, or fungal bio-membranes and bacterial, viral, or fungal infections in situ. The DC current can also be used to include a perimeter current zone or "fencing" around the infection to ensure that the entire infection has been treated.

In another aspect of the invention, a method is described to deliver monophasic or biphasic ascending or descending exponential, ramp, square, or damped sinusoidal waveforms which are most efficient with respect to treating bacteria, viruses, or fungus that cause infections in the bone or tissue by using phased array amplifiers where any three or more amplifiers and their respective electrodes may be driven differentially as to draw current through selected current pathways or different angular perspectives within the bone or tissue infection. Also, any one amplifier may be driven differentially to any of the other amplifiers in the array sequentially and/or simultaneously using the same arbitrary waveform. or any amplifier may be driven differentially to any of the other amplifiers sequentially and/or simultaneously using different arbitrary waveforms at different or equal voltage and current amplitudes. By use of this approach, many combinations of DC electrical current deliveries are possible and can be selected by the surgeon based upon individual patient requirements for infection destruction within a three-dimensional construct.

In another aspect of the invention, the phase array amplifiers will process any waveform and voltage amplitude through the mass as directed and selected by the surgeon, such as ascending or descending exponential, ramp, curved, damped sine, square, sine, triangle, saw tooth, etc. The voltage amplitude range shall be from about 0V to about +/−100V whereby DC voltages and currents can be delivered through the amplifier array in or out of phase with respect to the input signals as commanded by the microcontroller or FPGA.

In another aspect of a method of the invention, the method is carried out with differentially driven amplifiers, rather than a single current path or using the devices that deliver current and energy across one or more current pathways, but that cannot dynamically and proportionally alter and steer the voltage and current amplitude through each pathway in three dimensions.

In another aspect of the invention, a method can treat bacterial, viral, or fungal infections in, intra-medullary or around bone and/or joint implants.

In another aspect of the invention, a method of treating bone or tissue infection comprises delivering mono or biphasic square waves, ascending or descending exponential, ramp or square waveforms which are most efficient with respect to the cell conduction by using a phased array amplifiers where any two, three, or more amplifiers and their respective electrodes may be driven differentially and proportionally as to draw current through selected current pathways or different angular perspectives with the infection in three dimensions.

In another aspect of a method or apparatus of the invention, any one amplifier may be driven differentially to any of the other amplifiers sequentially and/or simultaneously using the same arbitrary waveform. Alternatively, any one amplifier may be driven differentially to any of the other amplifiers sequentially and/or simultaneously using individual and different arbitrary waveforms at different or equal voltage and current amplitudes.

In another aspect of a method of the invention, a positive pulse may use a square wave and a negative pulse may use a ramp waveform, or any waveform shape either in or out of phase using DC currents. This allows the waveform shapes to be mixed and matched to achieve optimum treatment results.

In another aspect of a method of the invention, the surgeon can select pre-programmed and pre-defined software waveform protocols, wherein many combinations of current deliveries are possible based on individual patient requirements for treatment of bone or tissue infections.

In another aspect of a method of the invention, the individual requirements are selected from the software protocol based on various medical criteria as defined by the surgeon with the goal of destroying infection while avoiding collateral damage in the bone or uninfected host tissue.

In another aspect of a method or apparatus of the invention, waveform protocols are pre-programmed and pre-defined and are loaded into a processor memory for quick execution.

In another aspect of a method or apparatus of the invention, 100 or more protocols can be stored for a surgeon to select from the computer menu.

In another aspect of a method or apparatus of the invention, arbitrary waveforms can be delivered to multiple electrode configurations, and multiple sequential or simultaneous three-dimensional current paths can be employed.

In another aspect of a method or apparatus of the invention, the phased array amplifiers will process any waveform through the mass directed by a surgeon such as ascending or descending exponential, ramp, square, sine, triangle, ramp or saw tooth, in DC positive or negative pulses.

In another aspect of a method or apparatus of the invention, monophasic or biphasic sequential or simultaneous current pulses are in the range of from about 0 mS to about 10 S or longer positive and negative time periods, in or out of phase respectively.

In another aspect of the invention, an apparatus for eradicating or reducing bacterial, viral, or fungal infections in bone or tissue comprises a means for dynamically and proportionally DC current steering or selecting two or more current vector paths sequentially or simultaneously through phased array amplifiers and electrode delivery system for infection treatment.

In another aspect of an apparatus of the invention, any one amplifier may be driven differentially to any of the other amplifiers simultaneously using the same arbitrary waveform. Alternatively, any one amplifier may be driven differentially to any of the other amplifiers sequentially using individual or different arbitrary waveforms at different or equal voltage and current amplitudes, as well as varying pulse-widths to a achieve desired treatment and ES therapies.

In another aspect of the invention, electrode shafts will be designed such that the surgeon can easily see the difference between the platinum conductive bands and the non-conductive sections of the electrode shafts using existing ultrasound equipment. This facilitates the alignment of the electrodes relative to the bone or tissue infection of interest in three dimensions.

In another aspect of the invention, a method of eliminating or reducing a bacterial, viral, or fungal infection in bone or tissue within a patient's body comprises dynamically and proportionally steering current vectors to treat or apply ES to the infection.

In another aspect of the invention, a method of treating or reducing a bacterial, viral, or fungal infection in bone or tissue within a patient's body comprises dynamically and proportionally steering current vectors to a predetermined defined area to electrically treat or apply ES to the infection to alleviate the condition.

In another aspect of a method of the invention, three or more electrode shafts are positioned in or around the bacterial, viral, or fungal infection in bone or tissue and DC voltages applied to the electrodes are varied to steer current vectors dynamically and proportionally through the bone or tissue infection.

In another aspect of a method of the invention, the bone or tissue infection is electrically treated or ES is applied to destroy or inactivate all, or at least reduce infection, within the bone or tissue.

In another aspect of a method of the invention, a microprocessor- or FPGA-controlled electronic amplifier array generates signals to produce dynamically and proportionally steered DC current vectors under software control using a computer.

In another aspect of a method of the invention, the microprocessor or FPGA manages the DC voltage, current, pulse-widths, arbitrary waveforms, power in watts and thermal data and directs the phased array amplifiers drive voltage amplitudes.

In another aspect of a method of the invention, an ascending ramp will generate a rate of change in voltage slower than the leading edge of a square waveform also known as a slew rate.

In another aspect of a method of the invention, the current vectors create a treatment zone within the bone or tissue infection which is the summation of intersecting current vectors to induce an additive DC current at the intersection of crossing vectors.

In another aspect of a method of the invention, and if hyperthermia is required and selected, the AC current vectors uniformly elevate the bone or tissue infection area to a temperature of from about 38° C. to no more than 48° C. More specifically, the bone infection area is heated to a temperature from about 38° C. to no more than about 48° C., for the purpose of protecting the integrity of the bone, for from about 5 to about 30 minutes or until all infection within the bone is destroyed, and the tissue infection area is pre-heated to a temperature from about 38° C. to no more than about 48° C. for from about 5 to about 30 minutes or until all infection within the tissue is destroyed. Any hyperthermia treatment will be held at a maximum tolerance of +/−1 degree C. by the microcontroller and software commands.

In another aspect of a method of the invention, a bacterial, viral, or fungal infection within or around a bone or within a tissue is treated.

In another aspect of the invention, a system for treating a condition or infection within a patient's body comprises:
  three or more electrode shafts;
  a microprocessor or FPGA for generating instructive signals; and
  an amplifier for receiving instructive signals from the microprocessor or FPGA and generating signals to the electrodes,
  wherein voltages of the electrodes are varied to dynamically and proportionally steer current vectors to and through the bone or tissue infection to resistively treat the infection with ES.

In another aspect of a system of the invention, the microprocessor or FPGA contains protocols to permit a surgeon using a computer menu to select a particular protocol.

In another aspect of a system of the invention, the system comprises three electrode shafts, each electrode shaft having platinum bands or contact points also known as "apertures" for conduction of the electrical therapies.

In another aspect of a system of the invention, each electrode shaft has a diameter of from about 1 mm to about 1.5 mm or about 0.039 inch to about 0.062 inch in diameter.

In another aspect of a system of the invention, each electrode has a current and thermal sensor.

In another aspect of a system of the invention, an ascending ramp will generate a rate of change in DC voltage that is slower than the leading edge of a square waveform.

In another aspect of a system of the invention, by using an amplifier array in conjunction with a microprocessor or FPGA, current can be focused in any specific area within a mass by proportionally varying the voltage amplitude and pulse-widths between electrodes to dynamically shift or steer a treatment zone anywhere in the bone or tissue infection in three dimensions, without moving the amplifier electrodes, to ensure destruction of bacterial infections within or around bone or tissue.

In another aspect of a system of the invention, the materials and construction of the electrode shafts and electrodes will be such that the difference between the conductive aperture portion of the electrodes and the non-conductive electrode shafts will be readily apparent by use visually and using conventional ultrasound equipment.

In another aspect of a method of the invention, a method of treating the bone or tissue infection within a patient's body comprises dynamically and proportionally steering current vectors around the perimeter of a bone or infected tissue to destroy the infection around or within the bone or tissue.

In another aspect of the invention, a system for treating a bone or tissue infection within a patient's body comprises:
three or more electrode shafts that define an area, wherein each electrode shaft has at least one platinum electrode band positioned along the shaft;
a microprocessor or FPGA configured to generate instructive signals that are DC arbitrary waveforms of a frequency of from about 15 KHz to about 25 KHz; and
phased array amplifiers are configured to receive instructive signals from the processor and to deliver signals to the platinum electrode bands,
wherein the microprocessor or FPGA is configured to control the amplifier array in such a way as to proportionately vary the voltage amplitude of signals to the electrode bands to dynamically steer and focus ionic current vectors to create and steer a treatment zone anywhere in three dimensions within the area between the electrode shafts, without moving the electrodes, to electrically treat and destroy all bone or tissue infection bacteria and bio-membranes while sparing host tissue and bone.

In another aspect of a system of the invention, the microprocessor or FPGA contains pre-programmed protocols to permit a medically trained operator to select a particular protocol for treating a bone or tissue infection.

In another aspect of a system of the invention, each electrode shaft has at least one platinum band or contact point.

In another aspect of a system of the invention, the microprocessor or FPGA samples and analyzes DC current and thermal data from the current and thermal sensors and manages the amplifier-delivered energy by adjusting voltage amplitudes and pulse-widths of arbitrary waveforms delivered to the electrode bands.

In another aspect of a system of the invention, the materials and construction of the electrode shafts and electrode band(s) will be such that visual surface contrasts of the electrode shafts and the electrode band(s) can be differentiated by a medically trained operator visually or by using conventional ultrasound or other imaging equipment.

In another aspect of a system of the invention, all the ionic current vectors intersect and combine to generate controlled and focused DC current treatment and therapies.

In another aspect of the invention, a system is configured to electronically steer the ionic current vectors using AC voltage and current to uniformly elevate areas of the bone or infected tissue to a temperature of from about 38° C. to no more than 48° C. More specifically, the bone infection area is heated to a temperature from about 38° C. to no more than about 48° C., for the purpose of protecting the integrity of the bone, for from about 5 to about 30 minutes or until all bacterial infection within the bone is destroyed or neutralized, and the tissue infection area is heated to a temperature from about 38° C. to no more than about 48° C. for from about 5 to about 30 minutes or until all infection within the tissue is destroyed or neutralized.

In another aspect of a system of the invention, a system further comprises an X-Y grid block, wherein three or more electrode shafts with platinum electrode band(s) will be capable of being inserted into holes within the grid block for the purpose of accurately inserting the electrode shafts as to ensure correct physical positions for each electrode during the treatment while an ultrasound video is used simultaneously as a mechanical guide to treat the bone or tissue infection.

In another aspect of the invention, a system for treating bone or tissue infection within a patient's body comprises:
three or more electrode shafts that define an area, each shaft having at least one platinum electrode band positioned along the shaft;
a microprocessor or FPGA configured to generate instructive signals that are DC level, arbitrary waveforms.
an amplifier array configured to receive instructive signals from the micro-processor or FPGA and to deliver signals to the platinum electrode band(s),
wherein the microprocessor or FPGA is configured to control the amplifier array in such a way as to proportionately vary the voltage amplitude of signals to the electrode band(s) to dynamically steer and focus ionic current vectors to create and steer a treatment zone anywhere in three dimensions within the area between the electrode shafts and around the perimeter of the bone or infected tissue using a fencing technique, without moving the electrodes, to destroy bone or tissue infection.

In another aspect of the invention, a system for treating a bacterial, viral, or fungal infection in bone or tissue within a patient's body comprises three or more electrode shafts that define an area, each shaft having at least one electrode band positioned along the shaft, a microprocessor- or FPGA-controlled electronic phased array amplifiers which are configured to deliver signals that are DC arbitrary waveforms of from about 15 KHz to about 25 KHz, to the electrode band(s), wherein the computer-controlled microprocessor or FPGA is configured to control the phased array amplifiers in such a way as to proportionately vary the voltage amplitude of signals to the electrode bands to dynamically steer and focus ionic current vectors to create and create a treatment zone anywhere in three dimensions within the area between the three or more electrode shafts, without physically moving the electrodes, and wherein bone or tissue infection is electrically treated while eliminating damage to the host bone and tissue.

In another aspect of a system of the invention, each electrode shaft has at least one current and one thermal sensor to provide feedback to the processor.

In another aspect of a system of the invention, the temperatures of the thermal sensors are monitored, and the current delivered to each electrode band is monitored.

In another aspect of a system of the invention, the combination of thermal and current measurements is fed into an algorithm the processor uses to vary the voltage amplitude.

In another aspect of a method of the invention for treating bone or tissue infection within a patient's body, the method comprises:

positioning three or more electrode shafts that define an area in or around bone or infected tissue, each shaft having at least one electrode band positioned along the shaft;

generating instructive signals from a microprocessor or FPGA that are DC arbitrary waveforms of from about 15 KHz to about 25 KHz; and receiving the instructive signals from the microprocessor or FPGA in phased array amplifiers configured to receive such signals and to deliver signals to the electrode band(s), wherein the microprocessor or FPGA is configured to control the amplifier array in such a way as to proportionately vary the voltage amplitude of signals to the electrode bands to dynamically steer and focus ionic current vectors to create and steer a treatment zone anywhere in three dimensions within the area between the electrode shafts, without moving the electrodes, to electrically treat the bone or infected tissue to ensure destruction of all infection in and around the bone or tissue.

In another aspect of a method of the invention, each electrode shaft has at least one platinum electrode band.

In another aspect of a method of the invention, the microprocessor- or FPGA-controlled electronic amplifier array generates signals to dynamically and proportionally steer current vectors under software control using a computer.

In another aspect of a method of the invention, the microprocessor or FPGA manages the voltage, current, pulse-widths, arbitrary waveforms current and thermal data, and makes adjustments to the amplifier drive voltage amplitudes manually or automatically.

In another aspect of the invention, a method of treating bone or tissue infection within a patient's body comprises dynamically and proportionally steering current vectors in three dimensions to a predetermined defined area comprising the infection to electrically treat or apply ES to the defined area to eradicate the infection.

In another aspect of a method of the invention, three or more electrode shafts comprise at least one electrode band on each shaft positioned around the defined area and voltages applied to the electrodes are varied to steer current vectors dynamically and proportionally to and through the defined area.

In another aspect of a method of the invention, three electrode shafts are used, and each shaft has at least one platinum electrode band.

In another aspect of a method of the invention, the defined area is treated sufficiently, or DC ES is applied to destroy, inactivate, or reduce infection within the defined area.

In another aspect of a method of the invention, the current vectors create a treatment zone within the defined area which is the summation of intersecting current vectors to induce an increasing current density to accelerate the destruction time of bacteria, viruses, or fungus.

In another aspect of a method of the invention, the defined area is around and or within a bone or tissue of a patient.

In another aspect of a method of the invention, the defined area is treated using 3 or 4 electrode shafts whereby the entire volume of bone or tissue within the energy field defined by the electrodes is treated to systematically deliver therapy to the defined area to destroy or inactivate the infectious cells contained within the defined area, thereby reducing or eliminating the infection.

In another aspect of the invention, a system for treating bacterial, viral, or fungal infection in bone or tissue within a patient's body, comprises:
three or more electrode shafts that define an area, each electrode shaft having at least one platinum electrode band positioned along the shaft;
a microprocessor or FPGA for generating instructive signals; and
phase array amplifiers for receiving instructive signals from the microprocessor or FPGA and generating signals to the electrode band(s),
wherein voltages of the electrodes are varied to dynamically and proportionally steer current vectors to and through the defined area to electrically treat the defined area to reduce or eliminate the infection.

In another aspect of a system of the invention, the system comprises three or more platinum electrode shafts, each electrode shaft having one or more platinum bands or contact points and each electrode having a current and thermal sensor.

In another aspect of a system of the invention, the system is suitable for treating a bacterial, viral, or fungal infection which occurs in the prostate, breast, liver, lungs, pancreas, kidneys, uterus, skin, ovaries, muscle, tissue or bone.

In another aspect of a system of the invention, voltage amplitude and pulse-widths between electrodes can be proportionately varied to dynamically shift or steer current vectors anywhere in the defined area in three dimensions, without moving the amplifier electrodes, to ensure proper resistive treatment.

In another aspect of the invention, a system for treating bacterial, viral, or fungal infection in bone or tissue within a patient's body comprises:
three or more electrode shafts that define an area comprising the infection, each shaft having at least one platinum electrode band positioned along the shaft;
a microprocessor or FPGA configured to generate instructive signals that are DC arbitrary waveforms of from about 15 KHz to about 25 KHz; and
phased array amplifiers configured to receive instructive signals from the microprocessor or FPGA and to deliver signals to the electrode band(s),
wherein the microprocessor or FPGA is configured to control the phased array amplifiers to proportionately vary the voltage amplitude of signals to the electrode bands to dynamically steer and focus ionic current vectors to create and steer a treatment zone anywhere in three dimensions within the defined area between the electrode shafts to resistively treat the defined area to reduce or eliminate the bone or tissue infection.

In another aspect of a system of the invention, each electrode shaft has one or more platinum bands or contact points as electrode bands and each electrode shaft has at least one current and thermal sensor to provide feedback to the processor.

In another aspect of a system of the invention, the temperatures of the thermal sensors are monitored, and the current delivered to each electrode band is monitored.

In another aspect of a system of the invention, the combination of thermal and current measurements is fed into an algorithm the microprocessor or FPGA uses to vary the voltage amplitude.

In another aspect of a system of the invention, the system is suitable for treating an infection which occurs in a breast, liver, lungs, pancreas, uterus, prostate, skin, ovary, bone, or elsewhere within or external to or transcutaneous on or in a patient's body.

In another aspect of a system of the invention, all the intersection of ionic current vectors are combined to generate controlled and focused DC treatment areas.

In another aspect of a system of the invention, the system is configured to electronically steer the ionic current vectors to uniformly heat and elevate all or portions of the defined area to a temperature of from about 38° C. to no more than 48° C.

In another aspect of a system of the invention, the system further comprises an X-Y grid block, wherein three or more electrode shafts with at least one platinum electrode band will be capable of being inserted into holes within the X-Y grid block while an ultrasound video is used simultaneously as a mechanical guide to accurately surround the bone or tissue infection that is to be treated.

In another aspect of the invention, a system for treating bone or tissue infection within a patient's body comprises:
three or more electrode shafts that define an area comprising the infection, each shaft having at least one platinum electrode band positioned along the shaft, and
computer microprocessor- or FPGA-controlled electronic phased array amplifiers which are configured to deliver signals that are DC arbitrary voltage and current waveforms of between about 15 KHz and about 25 KHz, wherein the computer-controlled microprocessor or FPGA is configured to command the phased array amplifiers in such a way as to proportionately vary the voltage and current amplitude of signals to the electrode bands to dynamically steer and focus ionic current vectors to create and steer a treatment zone anywhere in three dimensions within the area between the three or more electrode shafts, and
wherein the defined area is resistively treated sufficiently to reduce or eliminate the infection while eliminating damage within or surrounding host tissue.

In another aspect of the invention, a method for treating bone or tissue infection within a patient's body comprises:
positioning three or more electrode shafts that define an area comprising the infection, each shaft having at least one platinum electrode band positioned along the shaft;
generating instructive signals from a microprocessor or FPGA that are DC arbitrary waveforms of a frequency of from about 15 KHz to about 25 KHz; and
receiving the instructive signals from the microprocessor or FPGA in phased array amplifiers are configured to receive such signals and to deliver signals to the electrode bands,
wherein the microprocessor or FPGA is configured to control the phased array amplifiers to proportionately vary the voltage amplitude of signals to the electrode bands to dynamically steer and focus ionic current vectors to create and steer a treatment zone anywhere in three dimensions within the defined between the electrode shafts to deliver ES therapy to the defined area to reduce or eliminate the infection.

In another aspect of a method of the invention, each electrode shaft has at least one electrode band positioned along each shaft.

In another aspect of a method of the invention, the microprocessor- or FPGA-controlled electronic phased array amplifiers deliver signals to steer current vectors dynamically and proportionally under software control using a computer.

In another aspect of a method of the invention, the system and method are for treating a condition which occurs in a breast, liver, lungs, pancreas, uterus, prostate, skin, ovary, or bone, deep tissue or elsewhere within or external to a patient's body.

In another aspect of a method of the invention, each electrode shaft has at least one current and one thermal sensor to provide feedback to the processor.

In another aspect of a method of the invention, the microprocessor or FPGA samples and analyzes thermal data from the current and thermal sensors and manages the amplifier-delivered energy by adjusting voltage amplitudes and pulse-widths of waveforms delivered to the electrode bands.

In another aspect of a method of the invention using an AC voltage and current, the ionic current vectors are steered to substantially and uniformly elevate all or portions of the infected bone or tissue to a temperature of from about 38° C. to no more than 48° C.

In another aspect of a method of the invention, three or more electrode shafts with at least one electrode band positioned along each shaft will be capable of being inserted into holes within a X-Y grid block while an ultrasound video is used simultaneously as a mechanical guide to surround the defined area.

In another aspect of the invention, a method of treating a bacterial, viral, or fungal infection within a patient's body comprises dynamically and proportionally steering current vectors using differentially driven phased array amplifiers to a predetermined defined area comprising the infection to resistively heat the defined area or to use electrical stimulation (ES) to irradicate the infection.

In another aspect of a method of the invention, three or more electrode shafts comprising at least one electrode band on each shaft are positioned around the defined area and voltages applied to the electrodes are varied to steer current vectors dynamically and proportionally to and through the defined area.

In another aspect of a method of the invention, three electrode shafts are used, and each shaft has one or more electrode bands.

In another aspect of a method of the invention, the defined area is treated sufficiently to destroy or inactivate a bacterial infection within the defined area.

In another aspect of a method of the invention, the current vectors create a treatment zone within the defined area which is the summation of intersecting current vectors to induce treatment or an ES zone which operates from the electrolysis therapy whereby electrical DC current destroys bio-membranes and bacterial colonies by drawing more current than these biological cells can survive. These DC currents are typically in the range of 10 μA to about 3000 μA or 3 mA. Another mechanism thought to aid in the destruction of bacteria is an electrolysis effect whereby chlorine and or hydrogen peroxide are released and are effective in killing bacteria bio-membranes and bacterial colonies.

In another aspect of a method of the invention, the current vectors substantially uniformly elevate the defined area to a temperature of from about 38° C. to about 49° C.

In another aspect of a method of the invention, the defined area is infected within a bone of a patient or comprises infected tissue.

In another aspect of a method of the invention, the defined area is treated using 3 or 4 electrode shafts whereby the entire volume of bone or tissue within the three dimensional energy field defined by the electrodes is treated to systematically destroy or inactivate the infectious cells contained within the defined area, thereby reducing or eliminating the infection.

In another aspect of a method of the invention, reduction or elimination of the infection is accomplished using ES therapy without prescription drugs or surgery.

In another aspect of a method of the invention, the infection treated is in tissue, a bone, a joint implant, or a leg fracture.

In another aspect of a method of the invention, the infection treated is in an implant such as a hip, knee implant or leg fracture due to impact or accident.

In another aspect of a method of the invention, the infection results from diabetes or another disease.

In another aspect of a method of the invention, the method comprises treating a bed sore or another dermal or subdermal condition.

In another aspect of the invention, a system for treating bacterial, viral, or fungal infection within a patient's body comprises:
- three or more electrode shafts that define an area, each electrode shaft having at least one electrode band positioned along the shaft;
- a microprocessor or FPGA for generating instructive signals; and
- phased array amplifiers for receiving instructive signals from the processor and generating signals to the electrode bands,
- wherein voltages of the electrodes are varied to steer current vectors dynamically and proportionally to and through the defined area to electrically treat the defined area to reduce or eliminate the infection.

In another aspect of the invention, a system comprises three electrode shafts, each electrode shaft having one or more platinum bands or contact points and each electrode having a current and thermal sensor.

In another aspect of the invention, a system is suitable for treating bone or soft tissue infections which occur from bone fractures, injuries, knee or hip implants, deep irretraceable infections where antibiotics have failed and diabetic related infections or idiopathic causes which do not respond to antibiotic therapies alone.

In another aspect of a system of the invention, voltage amplitude and pulse-widths between electrodes are proportionately varied to dynamically shift or steer current vectors anywhere in the defined area in three dimensions, without moving the amplifier electrodes, to ensure proper treatment.

In another aspect of a system of the invention, each electrode shaft has one or more platinum bands or contact points as electrode bands and each electrode shaft has at least one current and thermal sensor to provide feedback to the processor.

In another aspect of a system of the invention, the temperatures of the thermal sensors are monitored, and the current delivered to each electrode band is monitored.

In another aspect of a system of the invention, the combination of thermal and current measurements is fed into the microprocessor or FPGA, which uses an algorithm to vary the voltage amplitude on command.

In another aspect of a method of the invention, three or more electrodes, typically four, are positioned substantially in a plane around the defined area and voltages applied to the electrodes are varied to steer current vectors dynamically and proportionally to and through the defined area.

In another aspect of a method of the invention, the electrodes each comprise a flat, flexible patch with a conductive metallic member.

In another aspect of a method of the invention, a bed sore is treated.

In another aspect of the invention, a dermal infection, such as a bed sore, especially a chronic bed sore, or other surface infection or condition, could be treated. Essentially the same system as described above could be used regarding the phased array amplifiers and/or the low DC current that would be employed. However, rather than an elongated electrode shaft, an electrode would comprise a short electrode with one band.

In another aspect of a method of the invention, the defined area is on or near the surface of a patient's skin.

In another aspect of the invention, a system for treating a bacterial, viral, or fungal infection on or near the surface of a patient's skin comprises:
- three or more electrodes that define an area, each electrode being a short electrode shaft with one band or an essentially two-dimensional electrode patch;
- a microprocessor or FPGA for generating instructive signals; and
- an amplifier for receiving instructive signals from the microprocessor or FPGA and generating signals to the electrode bands,
- wherein voltages of the electrodes are varied to steer current vectors dynamically and proportionally to and through the defined area to resistively heat the defined area to reduce or eliminate the infection.

In another aspect of the invention, each electrode has a current and thermal sensor.

In another aspect of a system of the invention, voltage amplitude and pulse-widths between electrodes can be proportionately varied to dynamically shift or steer current vectors anywhere in the defined area in three dimensions, without moving the amplifier electrodes, to ensure proper electrical treatment.

In another aspect of a system of the invention, the temperatures of the thermal sensors are monitored, and the current delivered to each electrode band is monitored.

In another aspect of a method of treating a bacterial, viral, or fungal infection within a patient's bone, low voltage electricity passes along an outer surface of a metal rod within the bone to electrically treat the infection or to use electrical stimulation (ES) to irradicate the infection.

In another aspect of a method of the invention, electricity is provided by an implantable power source such as a battery pack comprising one or more batteries or a magnetic power source.

In another aspect of the invention, a method for treating a bacterial, viral, or fungal infection within a bone or tissue in a patient's body comprises:
- inserting a metal rod into the bone;
- attaching a first metal screw into a first end of the metal rod;
- positioning another metal screw near the opposite end of the metal rod;
- attaching each screw to an implantable power source; and
- causing low voltage electricity to travel through the first screw along the outer surface of the metal rod to the second screw to irradicate the infection.

In another aspect of the invention, a method of treating an infection or potential infection within a patient's joint or bone comprises;
- positioning three or more electrode shafts comprising an electrode band on each shaft or three or more essentially two-dimensional electrode patches on the patient's skin around a joint or bone, and
- dynamically and proportionally steering current vectors using differentially driven amplifiers to a predetermined defined three-dimensional area comprising the infection or potential infection to electrically treat the defined area or to use electrical stimulation (ES) to irradicate the infection or prevent infection.

In another aspect of the invention, a system for treating a bacterial, viral, or fungal infection or potential infection within a patient's joint, tissue or bone comprises:

three or more electrodes that define an area, each electrode being a short electrode shaft with one band or an essentially two-dimensional electrode patch;

a microprocessor or FPGA for generating instructive signals; and an amplifier for receiving instructive signals from the microprocessor or FPGA and generating signals to the electrode bands, wherein voltages of the electrodes are varied to steer current vectors dynamically and proportionally to and through the defined area to resistively heat the defined area to reduce, eliminate, or prevent the infection.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 6B is a representation of an example of electrical current delivery between a plurality of electrodes that dynamically and/or proportionally steer electrical currents in three dimensions for the purpose of delivering electrical treatment and or an ES within bone or tissue with 100% coverage and no zones of infection missed by the treatment;

FIG. 10B is a cross-sectional view along line A-A in FIG. 10A.

DETAILED DESCRIPTION OF THE DRAWINGS

Figure 1:
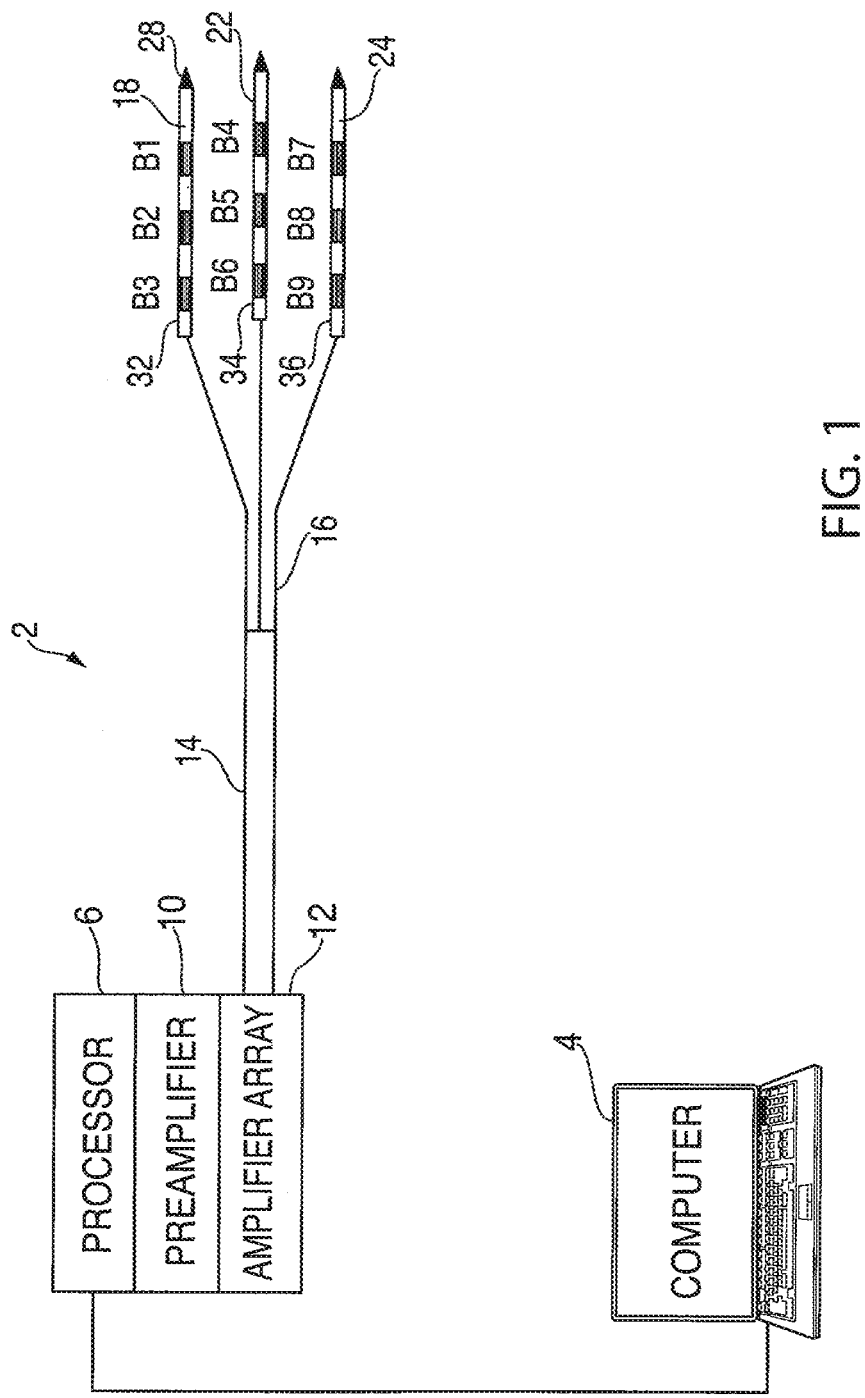
FIG. 1 is a schematic representation of one embodiment of a system useful according to the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

By definition, electrolysis of water is the decomposition of water ($H_2O$) into oxygen ($O_2$) and hydrogen gas ($H_2$) due to an electric current being passed through water. An electrolyte is any substance containing free ions that make the substance electrically conductive. The most typical electrolyte is an ionic solution, but molten electrolytes and solid electrolytes are also possible.

Commonly, electrolytes are solutions of acids, bases or salts. The human body is full of electrolyte solutions comprising, sodium, calcium, potassium, magnesium, etc., and all will conduct electricity.

If the above-described processes occur in pure water, $H^+$ cations will accumulate at the anode, and $OH^-$ anions will accumulate at the cathode. The negative hydroxyl ions that approach the anode mostly combine with the positive hydronium ions ($H_3O^+$) to form water. The positive hydronium ions that approach the negative cathode mostly combine with negative hydroxyl ions to form water. Relatively few hydronium (hydroxyl) ions reach the cathode (anode). This can cause a concentration over-potential at both electrodes.

This is applicable to the present invention. Dynamic and proportional current steering can be applied through an ionic solution or ionic mass. With regard to electrical currents, there are two basic conduction methods. First, electrons flow through conductive metals such as copper, silver, gold, steel, aluminum, etc. If AC is applied, the current flow will be positive to negative and negative to positive, alternating at the selected frequency between electrodes which become anodes and cathodes alternating respectively which causes heating. With DC, through a conductive metal, electrons flow from negative to positive with the cathode being the negative and the anode being the positive. Current will only flow in one direction, and it is not alternating although may be pulsed at a frequency in only one polarity.

The second major category is electrical currents through an ionic solution or ionic mass. If an electrical current is applied between two conductive electrodes while in distilled water or de-ionized water, little or no current will flow, whether AC or DC is applied. However, if one adds an ionic element or electrolyte solution into the distilled or de-ionized water, such as sodium, potassium, calcium, etc., or homogenizes them into a solid mass, they now become electrically conductive, but not in the same way as the electron flow described above.

FIG. 1 is a schematic overview illustrating bone or tissue treatment according to the present system. A system 2 comprises a computer 4 such as a laptop that provides the software waveforms and intelligent commands that direct a processor 6 which further processes commands from computer 4 to define and deliver the appropriate waveforms. Such waveforms include voltage amplitude, arbitrary waveforms, peak currents, and other electrical attributes which are then converted within processor 6 from digital to analog signals. The analog signals are then delivered to a preamplifier 10 which provides a small voltage gain in amplitude so that the waveforms selected for treatment can be distributed and delivered into an amplifier 12, which then provides voltage and current amplification at much higher levels. That allows for voltage and current waveforms to be delivered through the proximal end of a common multi-conductor cable 14, which is of a sufficient length to reach from an equipment rack (not shown) to a patient (not shown). Computer 4 contains a user-friendly menu so the surgeon may select which protocol he or she needs to treat infection in bone or tissue.

Cable 14 has a distal end 16 that is electrically connected to the proximal ends 32, 34, 36 of three cylindrical electrode shafts 18, 22, 24. Each electrode shaft 18, 22, 24 has at least three platinum electrode bands, identified here as bands B1 to B9. Each electrode shaft 18, 22, 24 has at its distal end a rigid dissolvable salt coating or substrate 28, to aid the surgeon with insertion into the patient. Such coating or substrate 28 will comprise a physiologically acceptable salt such as sodium chloride, potassium chloride, calcium chloride, or a functional equivalent. The coating or substrate 28 will partially or wholly dissolve during use, that is, after insertion into a patient's body.

At least the external surface of each electrode shaft 18, 22, 24, if not the entire shaft, comprises a rigid or substantially rigid non-conductive, sterilizable, and physiologically and medically acceptable material such as a polyethylene, polycarbonate, or polyurethane polymer or copolymer. The size of electrode shafts 18, 22, 24 can vary according to intended use and/or the size of the mass to be treated. For example, electrode shafts 18, 22, 24 could be from about 10 cm to about 40 cm, preferably from about 15 cm to about 30 cm, in length and, preferably from about 1 mm to about 1.5 mm, in diameter. Electrode bands B1 to B9 are spaced from about 2 cm to about 4 cm, preferably from about 2.5 to about 3.5 cm, apart, with a width of from about 0.5 cm to about 5 cm, preferably from about 1 cm to about 4 cm. One platinum plated conductive electrode may be preferred as one continuous electrode conductor.

Figure 2:
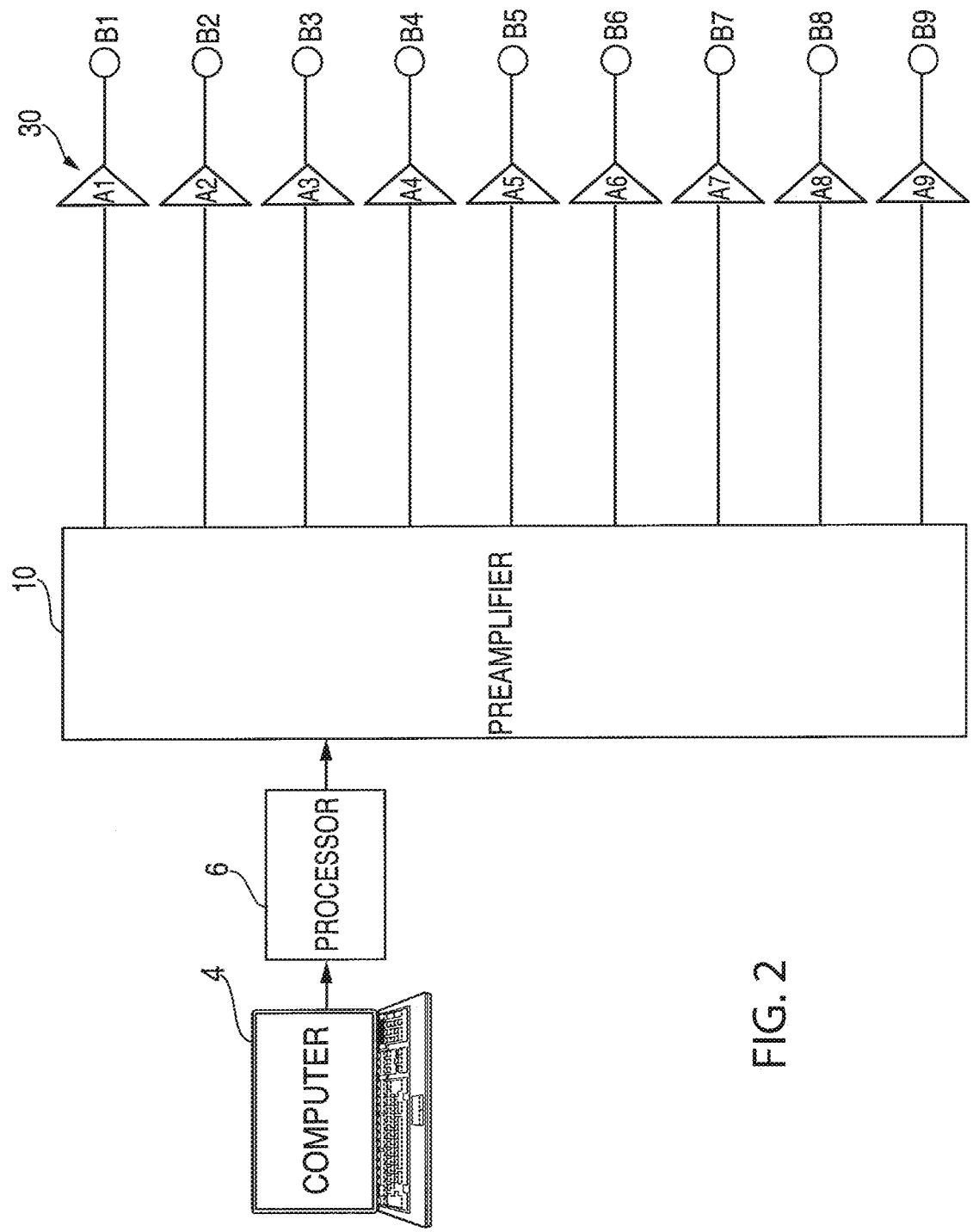
FIG. 2 is a detailed schematic representation of an aspect of a system according to the invention.

FIG. 2 is a detailed illustration of the system 2 shown in FIG. 1 where amplifier array 12 from FIG. 1 comprises a phased array 30 of six to nine amplifiers A1 to A9, based upon three or more electrode shafts having one or more platinum electrode bands each, which amplifiers A1 to A9 amplify the signals into electrode shafts 18, 22, 24 and corresponding electrode bands B1-B9. If the three electrode shafts each had four electrode bands, there would be twelve amplifiers A1 to A12. Three or four electrode bands on each shaft are consistent with 6 to 12 amplifiers, although the optimal and typical system comprises 6 amplifiers with one platinum electrode aperture per electrode shaft.

As illustrated, computer 4 sends digital signals to processor 6 and then into preamplifier 10, which distributes signals from processor 6 into as many preamplifier 10 output signals as are required for proper treatment of a bone infection 40.

The processor interprets the commands received from the computer and generates arbitrary waveforms of any shape, amplitude and pulse widths which are required to drive the amplifier array. Also, the processor converts the digital waveform information into analog waveform signals using a digital to analog converter or DAC. The analog waveform is amplified by the preamplifier. The preamplifier also serves as an electronic platform to mix and blend waveform signals prior to sending them onto the power amplifiers which make up the amplifier array as well as for thermal regulation and monitoring the current in each amplifier that makes up the array used for treatment.

Preamplifier 10 is required for two basic functions: First, it takes exceedingly small voltage signals and amplifies them to a level where a power amplifier phased array can be driven to the appropriate voltages and currents which are required to treat the bone infection of interest. And second, the preamplifier circuitry also serves as a platform for receiving the thermal feedback and current data in "real time" and communicates with the processor so the software may make minor adjustments to raise and lower voltage amplitudes which affect current levels and thus affect thermal control within and around the infection. Overall system feedback is important to affect the most successful medical outcome and for reasons of safety. The preamplifier in concert with the processor monitors all circuit functions so in the event of a component failure or power failure the system would shut itself down so as not to harm the patient being treated. Another aspect of this safety circuitry is it has the capability to run diagnostics on the amplifier array and make smart adjustments as required during therapy.

Amplifier array 30 comprises 3 to 12 or more amplifiers which are all identical in terms of circuit architecture. They are designed to deliver any voltage and current required to successfully treat bone infection using voltages from about zero to +/−100 VDC amplifier rail voltages from the power supplies. The voltage and current will be varied to achieve thermal averaging or a focused treatment zone of electrical therapy as an effective treatment system for bone and or tissue infections in a patient. The phased array amplifiers can be configured via software commands to operate in both constant voltage or constant current modes. Ultimately, having total control of treating with low current DC voltages of the bone or tissue infection of interest in three dimensions make this a useful tool for surgeons to increase cure rates and minimize amputations where antibiotics alone have failed to affect a cure.

The figures herein represent an exemplary depiction of three electrode shafts with three platinum electrode bands for delivering electrical currents within a construct of three dimensions for the purpose of creating electrical therapies to destroy a bone or tissue infection. It will be appreciated by those skilled in the art that there can be more than three electrode shafts, that each electrode shaft can have at least one, and perhaps as many as 4 to 8 or more electrode bands or contact points, and that each electrode shaft may not have the same number of electrode bands or contact points as another shaft. Also, for large bone, tissue and joint implant infection treatments, one long platinum conductive electrode band may be the preferred treatment selection.

Figure 3:
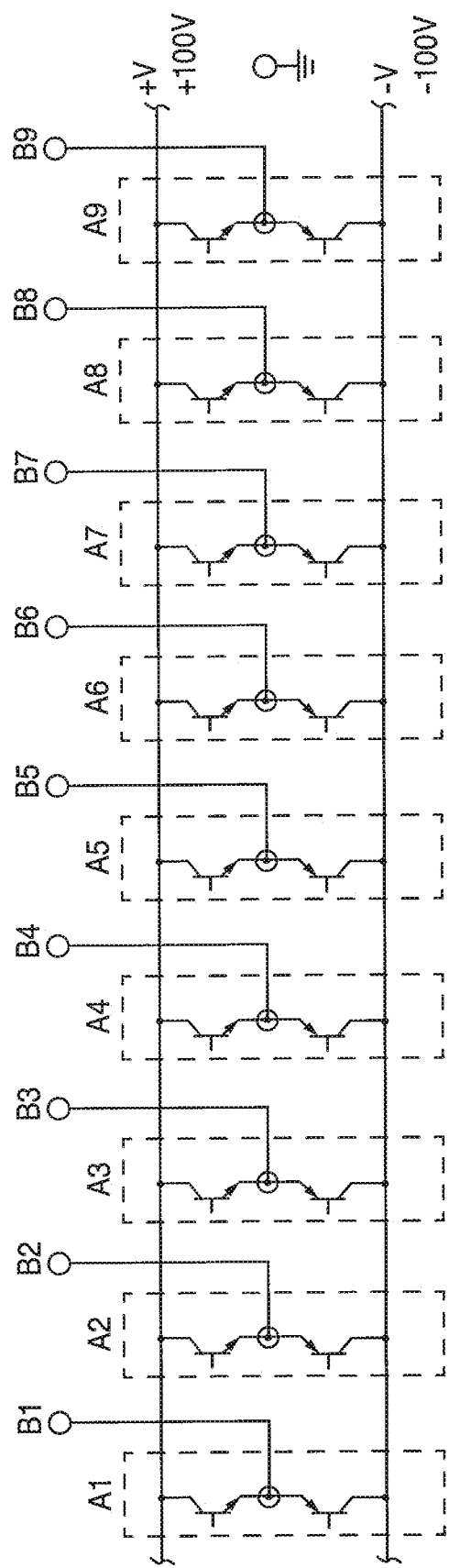
FIG. 3 represents a partial schematic of a differential amplifier phased array useful according to the invention.

FIG. 3 is a schematic illustration of the design architecture of a typical power amplifier array 30 comprising amplifiers A1-A9 in exemplary fashion. Each amplifier in array 30 differentially drives a signal into one of three electrode shafts 18, 22, 24 containing nine platinum electrode bands B1-B9 Amplifier array 30 is capable of delivering voltages and currents into electrode shafts 18, 22, 24 containing platinum electrode bands B1-B9 with an approximate voltage output of 0V to +/−100 VDC, which, when differentially driven, produces from about 0V to +/−200 VDC at a maximum current of less that 5 mA. This proportional voltage and current delivery system allow for precise treatment options for the desired outcome as commanded by the surgeon via the computer 4, processor 6, preamplifier 10, and amplifier array 30.

Figure 4:
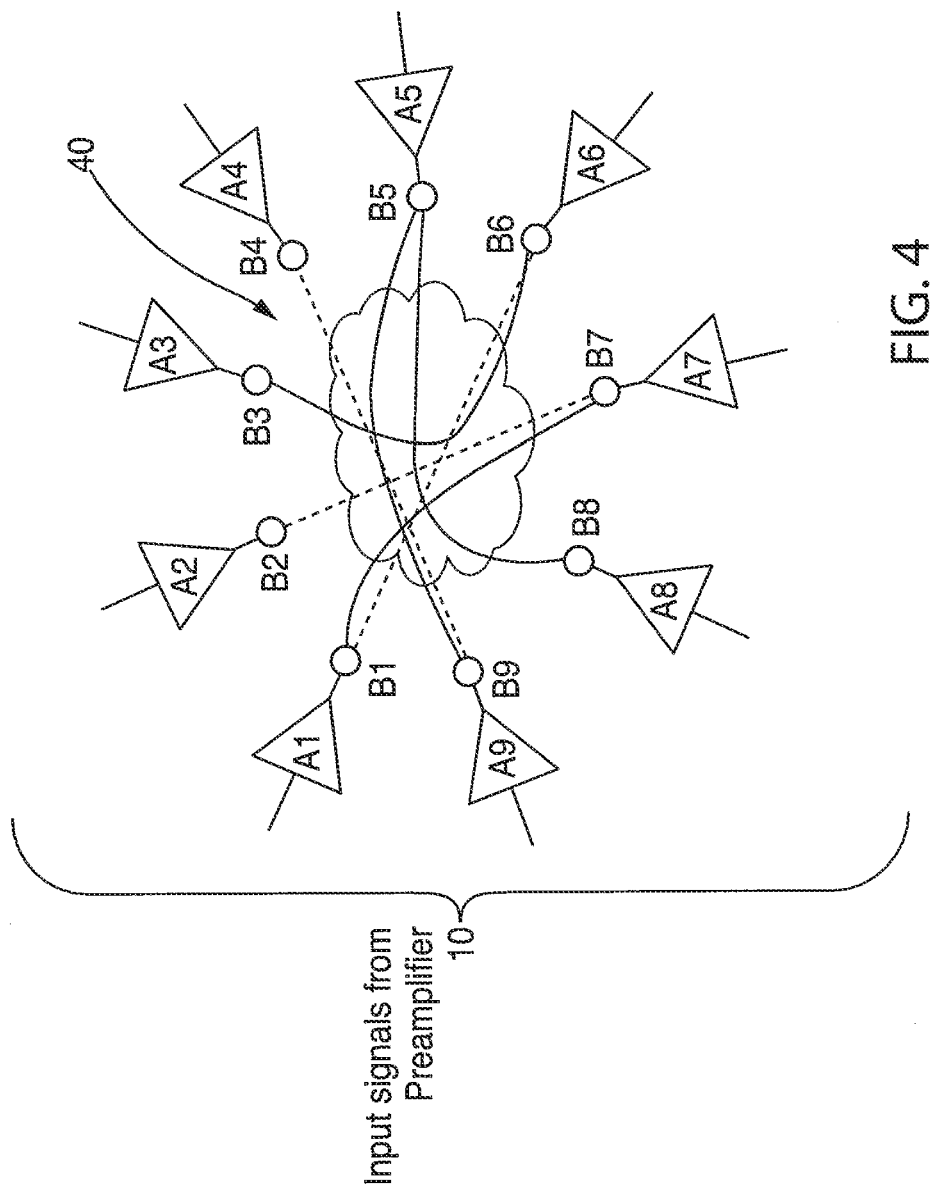
FIG. 4 is a schematic representation of one example of dynamic and proportional current steering according to the invention.

FIG. 4 is a schematic representation of an exemplary application of the amplifiers A1-A9 of array 30 in addition to electrode shafts 18, 22, 24 and their corresponding platinum electrode bands B1-B9, all delivering energy to and through an infected bone 40 or tissue. As depicted, voltage and current vectors may be delivered in straight lines or may be dynamically and proportionally steered as commanded by the surgeon via the computer 4, processor 6, preamplifier 10, and array 30 of amplifiers A1-A12.

Figure 5:
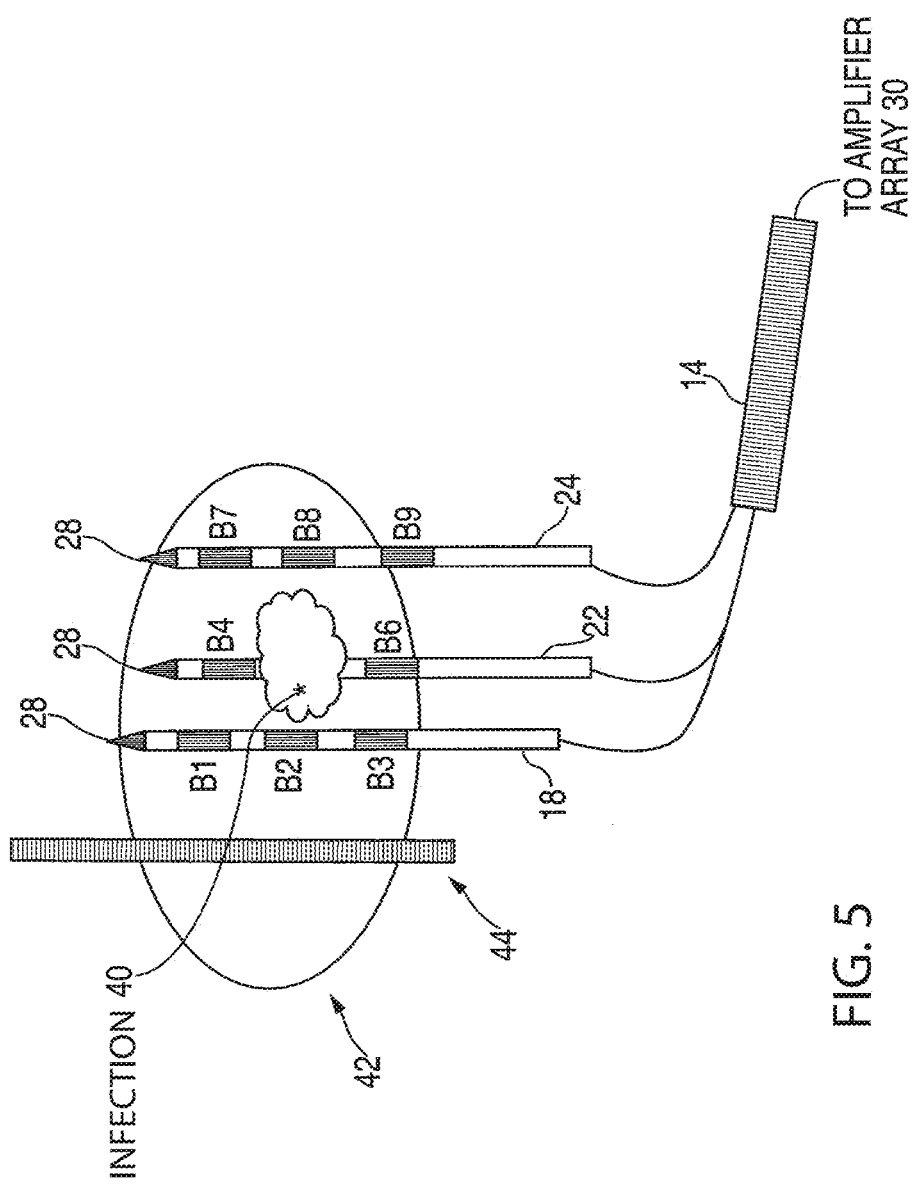
FIG. 5 is a schematic representation of use of a system according to the invention in treating a bone or tissue infection.

FIG. 5 illustrates an exemplary application for the treatment of an infection 40 within the construct of an organ, tissue, or bone in a male or female patient. Electrode shafts 18, 22, 24 are inserted into a patient, deep into the organ, tissue, or bone 42, for the purpose of aligning the electrode shafts 18, 22, 24. Corresponding platinum electrode bands B1-B9 receive signals from cable 14 and amplifiers A1-A9 to surround infection 40 in a 3-dimensional (3D) construct. Electrode shafts 18, 22, 24 are designed in such a way to contrast on ultrasound video to discriminate between the platinum electrode bands B1-B9 and the non-conductive, shaft portion of electrode shafts 18, 22, 24. This aids the surgeon with the appropriate placement of the electrodes.

Figure 6A:
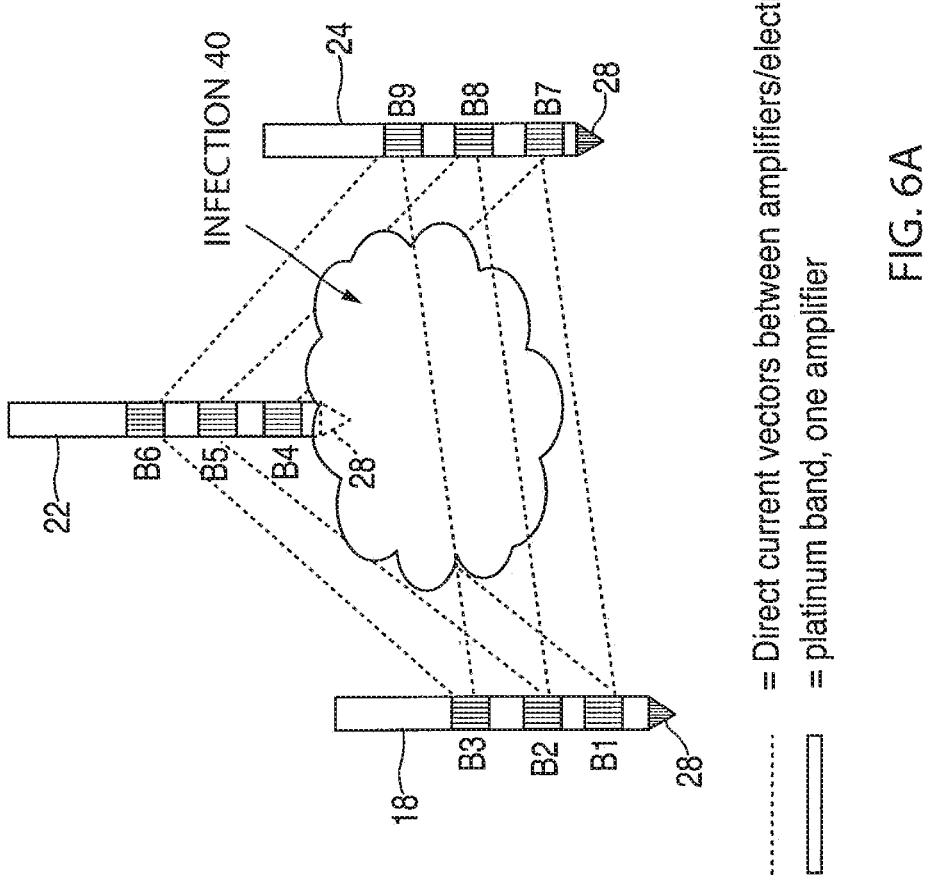
FIG. 6A is a representation of a traditional electrical current delivery between a plurality of electrodes that do not dynamically or proportionally steer electrical currents.

FIG. 6A is a schematic representation illustrating an exemplary two-dimensional system using electrode shafts 18, 22, 24 and their corresponding platinum electrode bands B1-B9, where voltages and currents are not dynamically or proportionally steered through the infected tissue and bone 40; rather, straight, point-to-point vectors will be generated. Using this two-dimensional fencing system, a defined perimeter may be formed to kill bacteria around an area as required for defining the area for treatment.

FIG. 6B is a schematic representation illustrating an exemplary three-dimensional system using electrode shafts 18, 22, 24 and their corresponding platinum electrode bands B1-B9, where voltages and currents are dynamically and/or proportionally steered as vectors 60 through the infected bone 40. The nine platinum electrode bands B1-B9 are capable of producing about 100 vectors 60 using this three-dimensional system. Since the voltages and currents are dynamically and/or proportionally steered through infection 40, 100% of the infection 40 of interest can now be subjected to treatment either in a thermal averaging method or by current averaging and or ES and proportionally commanding electrode shafts 18, 22, 24 to surround the infection 40 of interest in a three-dimensional (3D) construct. [Another benefit of using the software-commanded system is the ability to create and move an elevated zone of hyperthermia, 48C maximum] or ES through the infection 40 by applying the principle of delivering energy in six degrees of freedom, which represents three-dimensional heating of mass 40. Therefore, the infection contained within the bone 40 will be destroyed, providing an effective treatment. An additional or optional aspect or benefit of using the three-dimensional treatment system with dynamic and proportional steering of current vectors is the ability to surround or "fence" the perimeter of the infection 40 with treatment three-dimensionally.

Figure 6C:
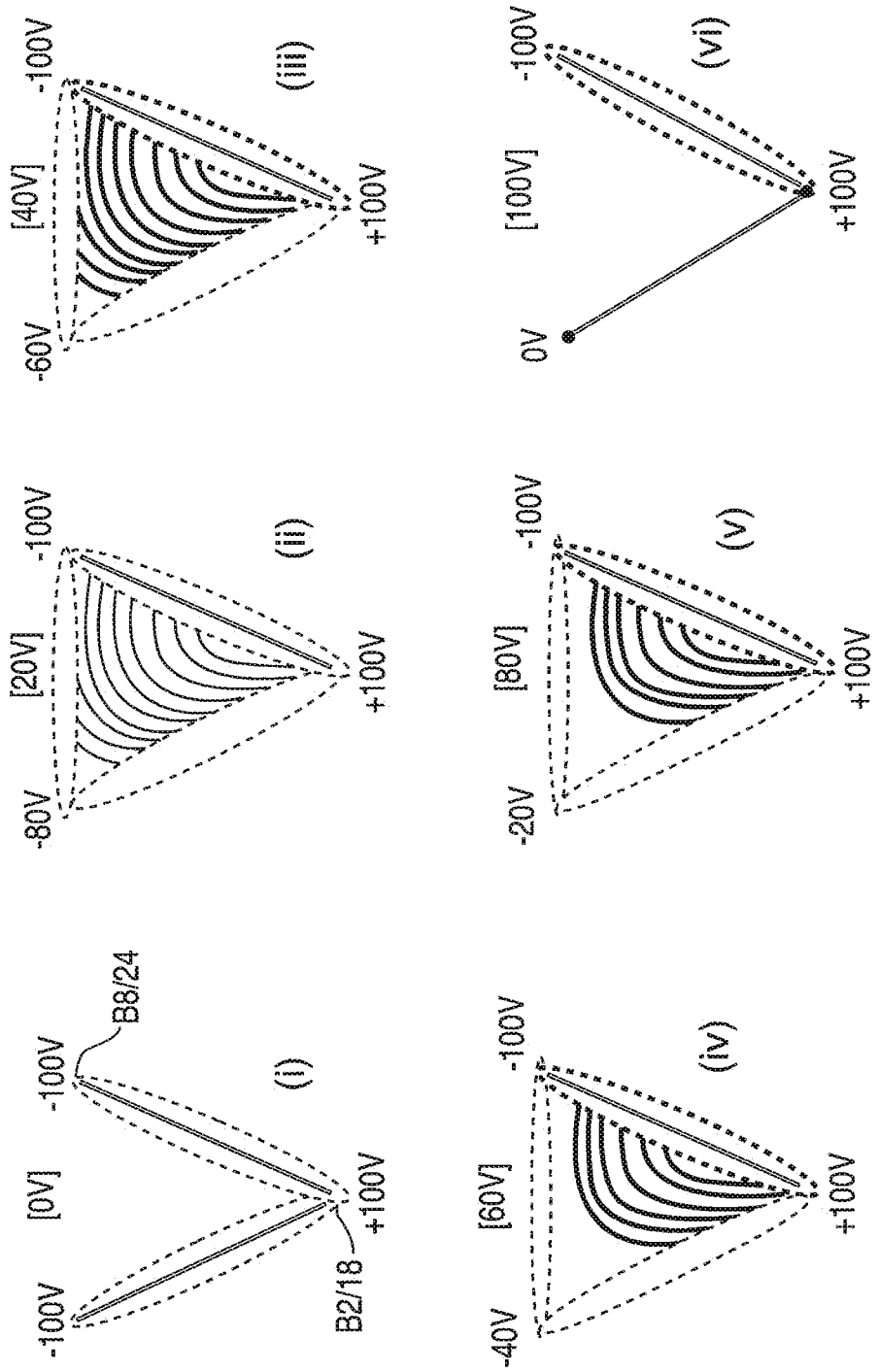
FIGS. 6C(i) to 6C(vi) are schematic representations of dynamic and proportional steering of DC current through amplifier phased arrays driven differentially through three electrodes.

FIGS. 6C(i) to 6C(vi) are schematic cross-sections of an exemplary phased array current steering pattern among electrode bands B2, B5, and B8 on electrode shafts 18, 22, and 24, respectively. As the voltage is commanded to be lowered on B5 by processor 4, there is a progressive shift in current flow as depicted in FIG. 6C(ii). The current between B2 and B5 begins to decrease, and because there is now a difference in voltage between B5 and B8, a current begins to flow between B5 and B8. As the voltage continues to decrease between B2 and B5, the current is proportionally steered through the bone or tissue infection 40 toward B8 as depicted in FIG. 6C(iii). The change in current flow in terms of time or rates of change is a function of the commands received from processor 4. If one applies this principle of operation to all nine bands, a true 3-dimensional tissue and bone infection may be treated, or ES applied equally or in a focused zone and moved within the infection via the microprocessor or FPGA commands. The current densities are shown with the darker areas having the higher current densities and the lighter shades have lesser current densities. Thus, voltage and current through an ionic mass deliver treatment as follows: Increasing voltage=increasing current=decreasing impedance=decreased treatment time of bacterial infections. Therefore, dynamic and proportional current steering occurs when voltages are raised and/or lowered between electrodes within an ionic solution or bone or tissue infection 40.

Figure 7:
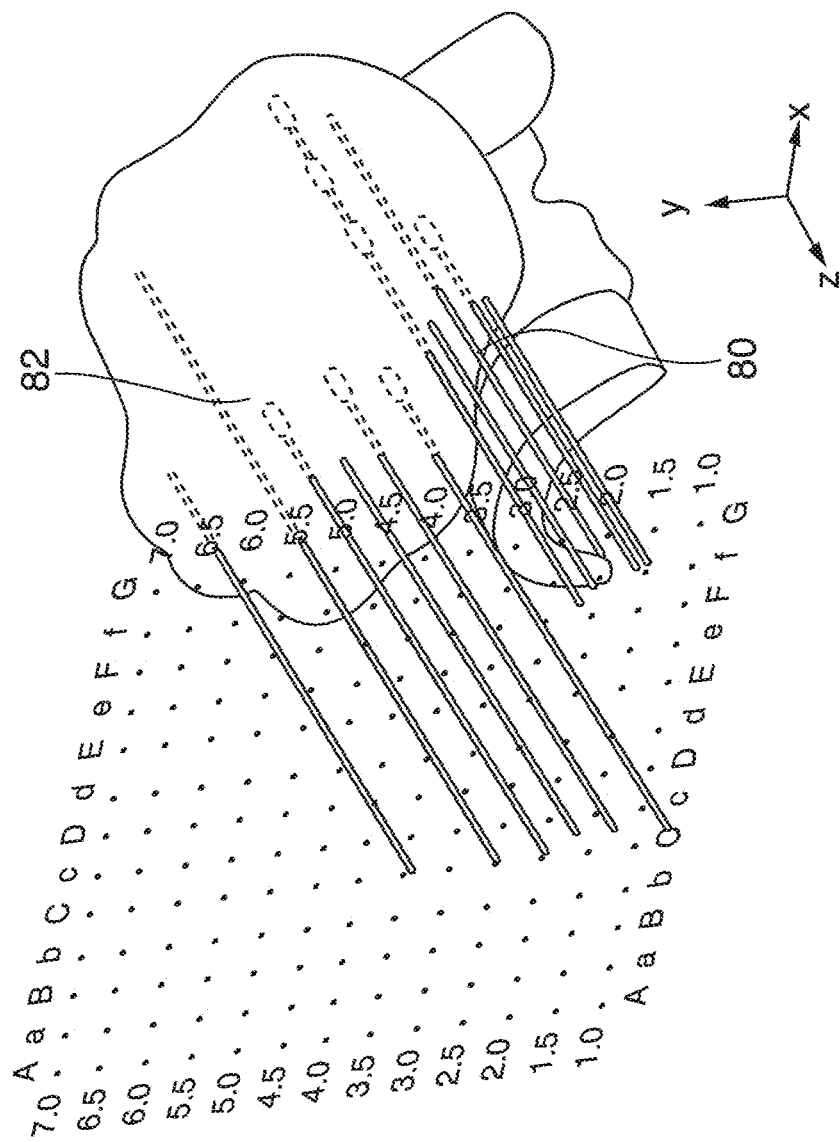
FIG. 7 is a schematic representation of electrode shafts that have been inserted into an infected bone or an area of infected tissue to treat, or optionally map, the infected bone or tissue.

FIG. 7 is a schematic representation of a mapping and treatment procedure where shafts 80 have been inserted into bone or infected tissue 82 to map and treat bone or tissue infections 40. Shafts 80, which can be biopsy probes, needles, or other longitudinally extending members that sense parameters or release chemicals, are typically inserted in predetermined patterns and orientations using an X-Y grid block or template so that the surgeon can determine the extent, that is, the width, depth, length, and shape, of infected area 82, optionally in concert with the appropriate imaging and scanning devices. When the extent of an infection is determined, the shafts 80 can be withdrawn and three or more electrode shafts comprising one or more platinum bands as electrodes (not shown here) can be inserted to dynamically and proportionally steer current vectors through the infected area 40, as described above.

Alternatively, some or all of shafts 80 may be a combination of biopsy probe or needle and an electrode shaft so that once appropriate imaging and scanning maps and precisely locates the bone or tissue infection, the site can be treated using DC voltages and currents as represented in the present invention stated herein. Thus, in accordance with an embodiment of the invention, three or more of shafts 80 comprise one or more electrode bands so that current vectors can be dynamically and proportionally steered to destroy the bone or tissue infection 40 discovered during the mapping procedure or scans.

It is within the scope of the invention that three or more electrode shafts, preferably from 4 to 6 electrode shafts, with at least one electrode band each could be used to define a three-dimensional treatment area. For example, a bone having an infected area 40 could be treated by positioning electrode shafts adjacent to the bone, internal to the bone, to create a three-dimensional shaped area that encompasses and treats the bone and or tissue infection 40. Electrodes may be designed and constructed as electrode shafts with conductive bands The same dynamic and proportional steering therapies may be employed to ensure all infections are cured and resolved medically.

Figure 8:
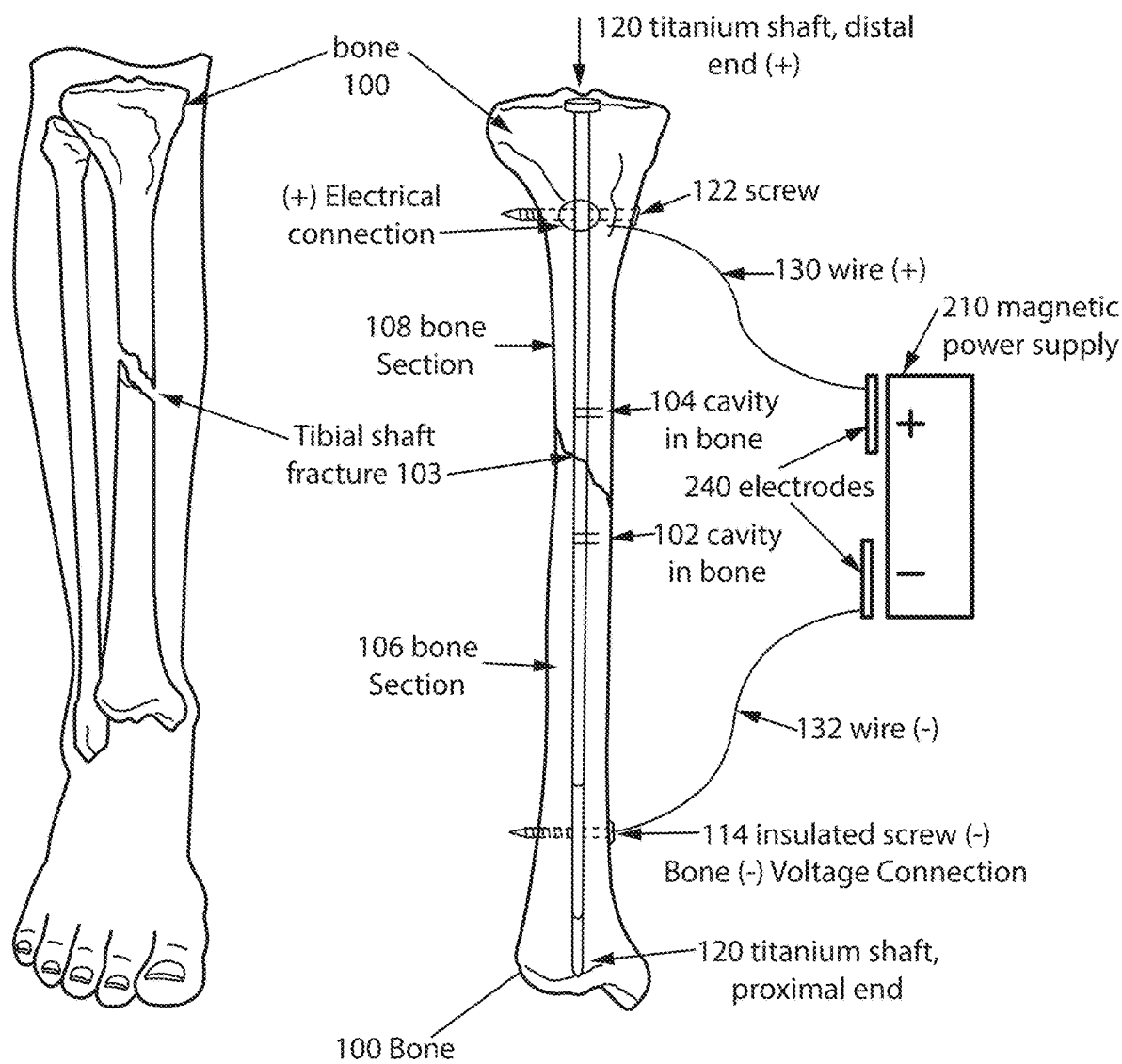
FIG. 8 is a schematic representation of a bone where electrodes have been attached to screws that are attached to or adjacent to opposite ends of a titanium rod inserted into a patient's leg bone to chronically prevent and or treat bacterial infections.

In another alternative embodiment, infections in a bone can be treated as shown in FIG. 8, where an elongated bone 100, such as a tibia, has been treated where cavities or holes 102 and 104 have been drilled or otherwise created in bone sections or fragments 106 and 108 for the purpose of mechanically repairing the fracture portion of the tibia bone 100. A titanium shaft 120 has been inserted into the tibia and sections 106 and 108 at the fracture area 103 have been connected together mechanically with various plates and/or screws, etc. (not shown). A metal screw or pin 114, preferably titanium, has been inserted into and attached to proximal end of titanium shaft area 120 adjacent to the negative (−) wire 132 but not in electrical contact with titanium shaft 120. At the distal end titanium shaft 120 a metal screw or pin 122, preferably titanium, is positioned and attached electrically to the positive (+) electrode using wire 130 to titanium shaft 120.

The arrangement shown in FIG. 8 is based upon the theory that a low voltage and current connected electrically to one end of titanium shaft 120 will conduct through and along the outer surface of titanium shaft 120 to treat or prevent infection within the wound across the entire length of shaft 120 and the infected area shall draw a very low DC current between and through the entire tibia bone that spans between the distal and proximal ends of the entire bone 100. Screw 114 and/or screw 122 will each be connected to its own source of electricity, the negative (−) electrode wire 132, screw 114 and screw 122 to a positive electrode and wire 130 (+) such as an implantable battery or a magnetic power source (MPS) 210. Wires 130, 132 would connect screws 114 and 122, respectively, to electrodes 240 on MPS 210. The voltage and current should be in the range of a few millivolts to about one volt and very small chronic electrical currents of microamps to about 1-4 ma. Particularly in the use of DC voltage and current the bio-membranes that protect bacterial colonies are vulnerable to destruction using very small DC electrical currents.

The basic idea here is a "powered" titanium screw that has either its own battery power source or an implantable power source. This system could be placed in a quick outpatient procedure by almost any general orthopedic surgeon on either side of the fracture/infection. Alternatively, the screw could be left in place and a simple tap/die system could be used to secure the electrode power pack onto the head of the existing screw. The device would start off with its DC current to disrupt biofilm/kill bacteria (possibly without even antibiotic use). Then, by adding a microprocessor device upgrade, the system could be transitioned to delivering a different software algorithm to induce bone growth/formation (of which there is significantly more literature, but still complete lack of mainstream adoption). Optionally an AI technology or beam steering therapy could be utilized to electrify the tibial nail/antenna array utilizing the screw/nail electrode construct to treat bone and tissue infections.

In an alternative embodiment of the invention, one or more titanium screws attached to a titanium rod could inductively receive power from, for example, a coil positioned around a patient's limb. The coil could be incorporated into a flexible substrate that could be fastened in place. Ends of the coil would be attached to a suitable external power source.

Figure 9A:
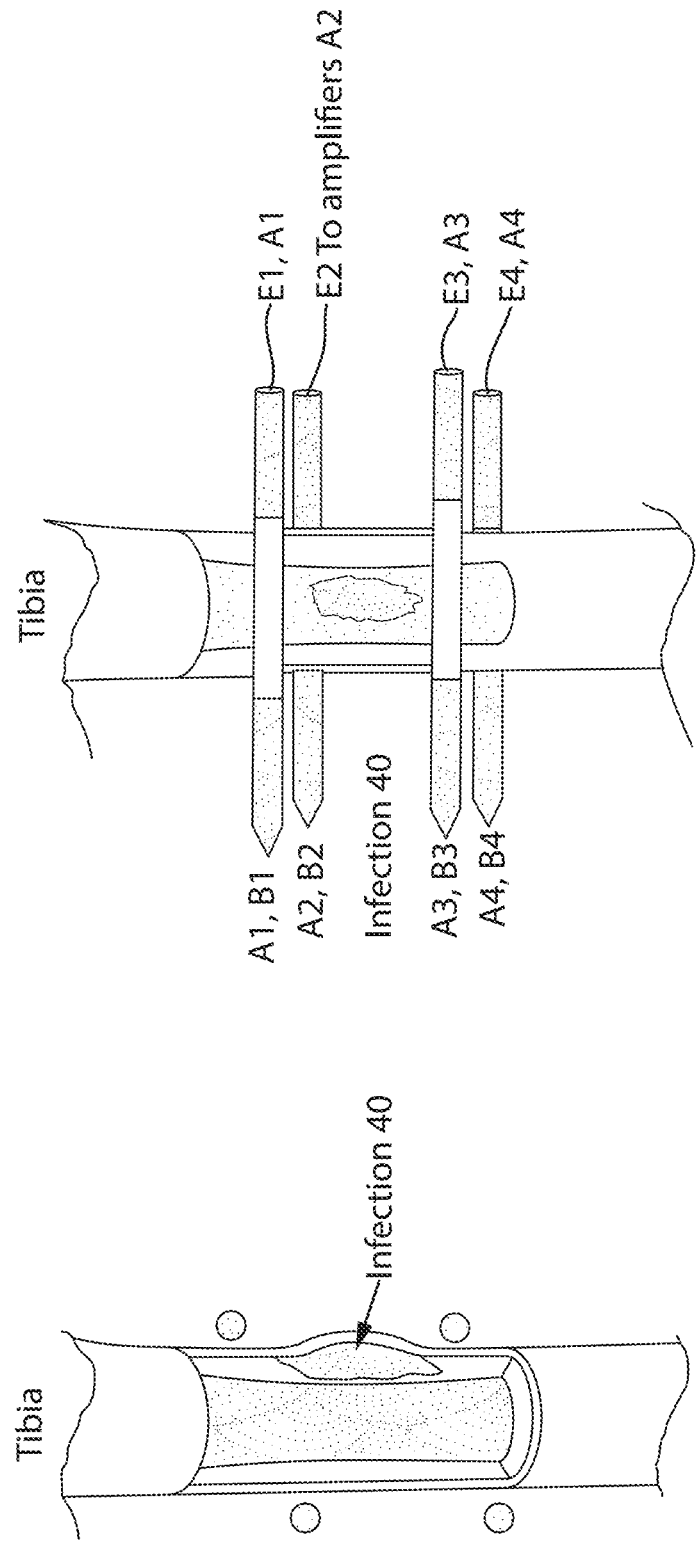
FIGS. 9A, 9B(i) to 9B(vi), and 9C show a three-dimensional example of how an infection will be treated using the current vectors that are time delivered between the electrodes that have commands delivered from the amplifiers and their respective electrodes as specified. Time periods are established by the software and microprocessor or FPGA.

FIG. 9A depicts a typical application of platinum plated electrodes inserted within an infected leg are whereby an infection is treated using DC currents that are dynamically and proportionally steered between electrodes E1/A1, E2/A2, E3/A3, and E4/A4 to treat infection 40.

FIGS. 9B($i$) to 9B($iv$) define the DC rotation phased array vector patters that are delivered to create software programmed time periods that establish anode and cathode zones for time periods long enough to establish the electrolysis effect as well as a definitive DC current flow between electrodes. In FIG. 9B($i$), electrode E1 is configured as the anode while electrodes E2, E3, and E4 function as cathodes, producing a set of directional current vectors radiating outward from E1. In FIG. 9B($ii$), the active anode shifts to electrode E2, while electrodes E1, E3, and E4 become cathodes, rotating the current vector field clockwise. In FIG. 9B($iii$), electrode E3 is set as the anode, and the remaining electrodes E1, E2, and E4 serve as cathodes. Finally, in FIG. 9B($iv$), electrode E4 assumes the anode role with electrodes E1, E2, and E3 acting as cathodes. These sequences are repeated through software-controlled logic via a microprocessor- or FPGA-driven amplifier array, allowing precise control over current steering. By rotating these anode and cathode zones for the correct number of seconds and minutes, for example, 10 seconds for each zone, the entire area or domain within the treatment area will be treated 100% by intersecting DC vectors over 40 seconds by the phased array amplifier system to destroy bacteria and eliminate the infection zone as defined in the treatment zone, as shown in a summation in FIG. 9B($v$). FIG. 9B($vi$) depicts the system using high voltage (HV) direct current using a 15 kHz square wave at up to 4 milliamps of current. For hyperthermia it needs to be an AC waveform, not DC. +/−20V amplitude square wave, the electrodes would change polarity at a 15KHz rate, and the PRF rotation would occur at approximately a 2KHz rate.

Figure 9C:
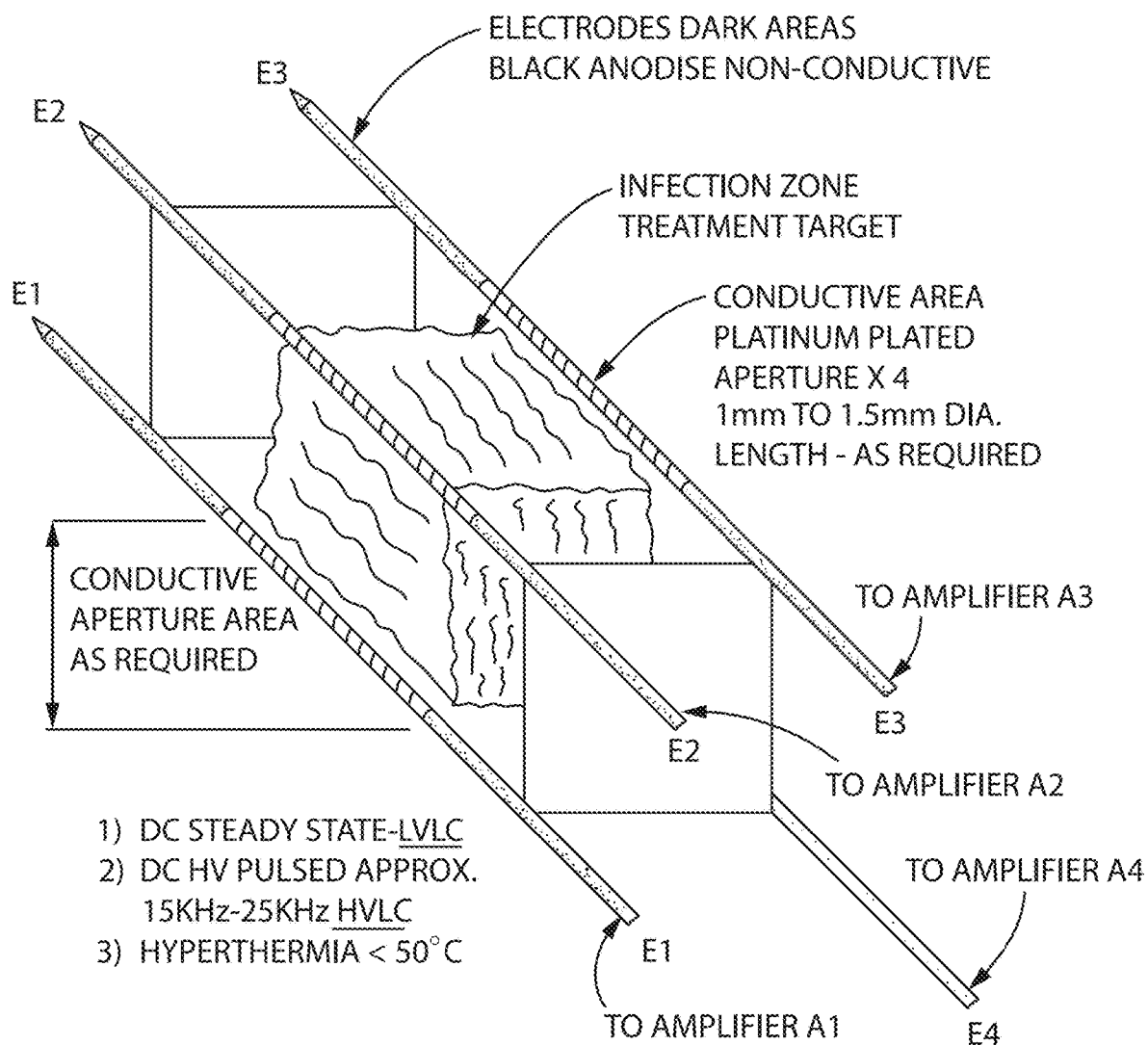

FIG. 9C depicts a three-dimensional example of how an infection can be treated using the current vectors that are delivered between the electrodes that have commands delivered from the amplifiers and their respective electrodes as specified in FIG. 9A. In this embodiment, a cubic treatment zone, the system is configured to operate sequentially across multiple treatment phases. It begins with a low-voltage, low-current direct current (DC) application across electrodes E1, E2, E3, and E4, followed by a high-voltage (HV), low-current (LC) pulsed DC waveform ranging between 15 kHz and 25 kHz. This may subsequently be followed by a controlled hyperthermia phase, maintaining temperatures below 50° C. to effectively eliminate infected tissue while minimizing the risk of damage to adjacent healthy tissue.

Each electrode E1, E2, E3, and E4 comprises a non-anodized, platinum-plated conductive zone designed to deliver energy precisely to a defined treatment area. Surrounding this is, for example, a black anodized, non-conductive boundary, which functions to restrict and localize the treatment field. The precise area of therapeutic delivery may be determined by the treating physician using imaging techniques prior to initiating treatment.

Figure 10A:
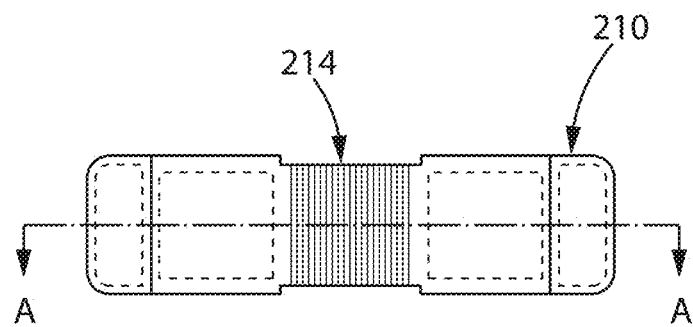
FIGS. 10A and 10B represent a magnetic power source.
Figure 10B:
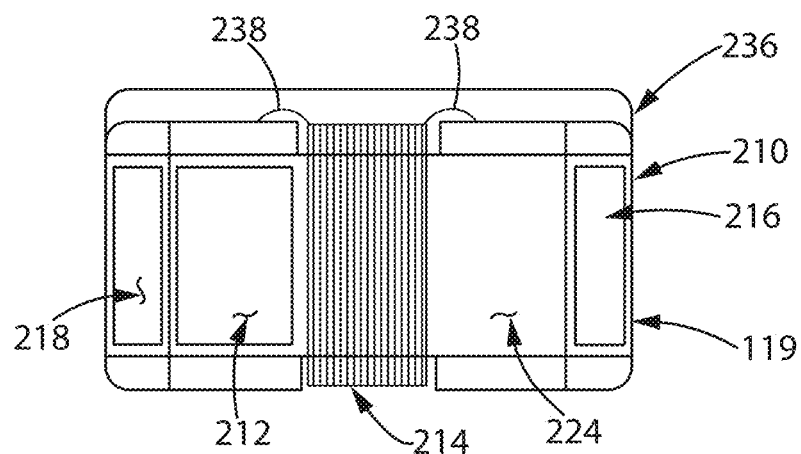
Figure 11:
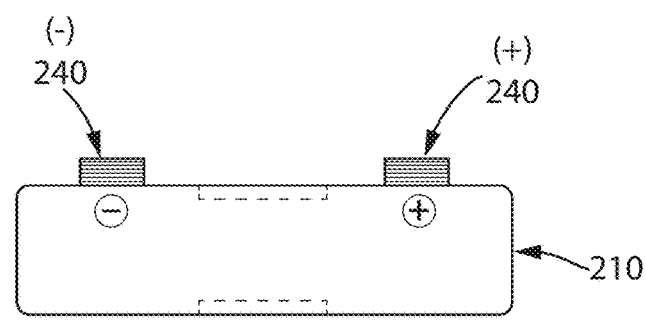
FIGS. 11 to 13 depict different views of a magnetic power source implanted adjacent to a titanium rod which reinforces the bone as it receives low voltage, low current therapy to treat infections from a trauma.
Figure 12:
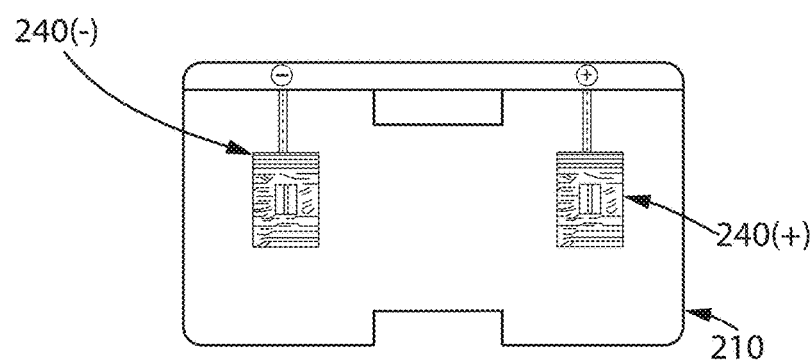
Figure 13:
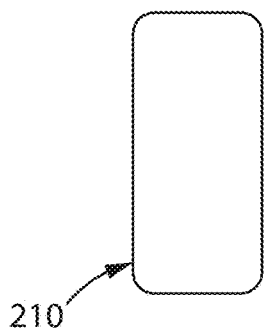
Figure 14:
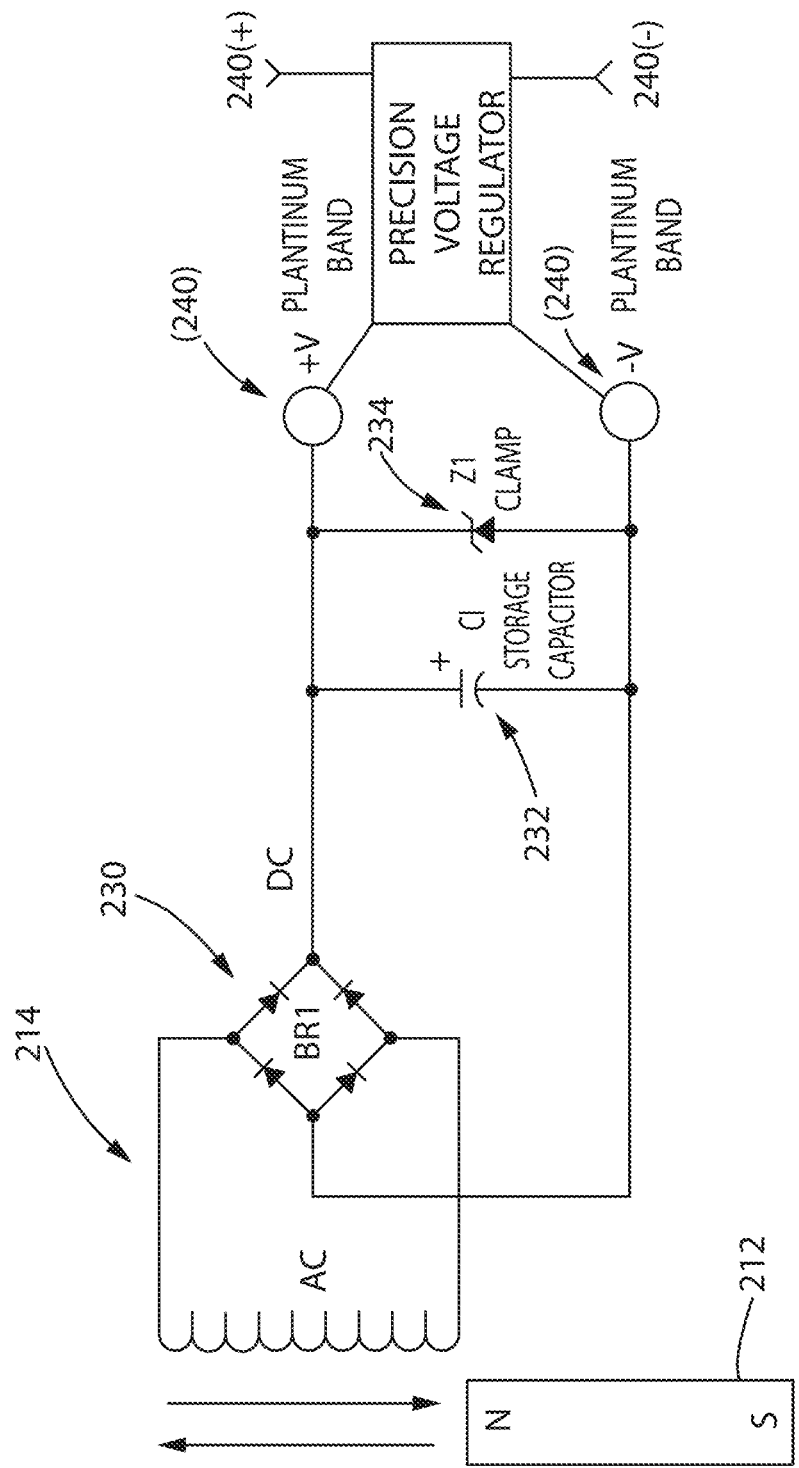
FIG. 14 is a schematic representation of a magnetic power source and the components that convert the AC voltage to a DC low voltage, low current.

The embodiment described above and represented in FIG. 8 is preferably used with a low power, implantable power supply. An example of such a power supply that does not require batteries is shown in FIGS. 10A to 14, which refer to a magnetic power source [MPS] device 210 in which a traversing or flying magnet 212 is employed using Faraday's Law of Electromotive Force [EMF] to create an electrical potential or voltage by moving a magnet through a coil 214 of wire with a specified number of turns. The traversing magnet 212 is captured in a cavity between two other magnets which are installed in fixed positions as to have their fields aligned as repelling magnets 216, 218 for the traversing magnet 212. On one end of the device the north pole of a fixed magnet 218 will be opposing the north pole of the traversing magnet 212 and on the opposite end of the device the south pole of the fixed magnet 216 will be opposing the south pole of the traversing magnet 212. This arrangement provides a traversing magnet 212 which will traverse or fly between both opposing fields within the device cavities without hitting the internal end walls of a case 222. [Magnetic poles or fields which are the same will repel and magnetic poles or fields which are opposites will attract.] Traversing magnet 212 shall have a coating of polytetrafluoroethylene or a similar material to reduce friction to near zero within the traversing chamber 224. As the traversing magnet 212 is propelled by walking, running or any other motion in the vectored direction of the device, the traversing magnet 212 passes through the wire coil 214 as shown in FIG. 10 to generate electrical energy.

The repelling magnets 216, 218 aid in the perpetual motion of the traversing magnet as to provide a DC voltage. This action produces an electrical alternating current [AC] which is then rectified through BR1 230 into a direct current [DC]. The DC voltage is then filtered by C1 232 to remove any AC ripple and is also used as a storage device, and keeps the DC voltage stable and quiet from noise to power the electrodes. Zener diode Z1 234 is used as an electrical clamp to keep the maximum voltage limited to a value expected to be from about 1 VDC to about 2 VDC. These components are housed in the electronics cavity 236. Coil wires 238 extend from wire coil 214 into electronics cavity 236.

When any limb or body movement is happening, the magnet power supply will generate from approximately 1 mVDC to about 12 VDC. The 12 VDC will then be regulated down to about 5 VDC. The regulated voltage output can be adjusted from a wireless commanded source such as a BlueTooth device. When exercise occurs such as walking or running, the expected voltage will rise to from about 1 VDC to about 5 VDC until Zener diode Z1 234 clamps the voltage at the selected peak voltage. These voltages provide the stimulus for DC ES therapy along the intended span between electrodes or screws to kill bacteria and destroy the biomembrane which protect the bacterial colonies. A post output voltage regulator may be added to deliver a more precise voltage and current therapy to maximize the destruction of bacteria, virus or fungus growth. Advantageously, the magnetic device MPS 210 will deliver the appropriate DC therapy as an implant that eliminates the requirement for implanted batteries, wires, or any other outside energy source by creating an electrical power source between electrodes. Also, advantageously, in the prevention mode, as a person exercises the output voltage of the MPS 210 increases, thereby providing an increased voltage that will be protective against any bacterial activity that may try to proliferate. The MPS 210 may be implanted wherever the therapy power source will be most effective in delivering the voltage and current. The surgeon may use brackets provided on the outer case of the MPS 210 to secure the MPS 210 device near or in close proximity to the titanium rod that is to be energized using electrodes 240+/−V as shown in the FIGS. 11, 12, and 13.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of treating a bacterial, viral, or fungal infection in a patient's bone or tissue, which method comprises:
    providing three or more electrode shafts, each electrode shaft having proximal and distal portions and each electrode shaft having at least one electrode band positioned around the distal portion of the electrode shaft;
    positioning the distal portions of the electrode shafts within the patient to define a defined area in the patient's bone or tissue comprising the infection;
    generating instructive signals from a microprocessor or FPGA that are received in an amplifier array comprising differentially driven phased array amplifiers and configured to receive such instructive signals and to deliver signals to the electrode bands; and
    dynamically and proportionally steering DC current vectors to the defined infected area to electrically treat the defined infected area to destroy biological membranes of the infection,
    wherein bacteria within a structure of the infection is eradicated or lessened while host tissue or bone is spared, and
    wherein the DC current vectors are in the range of from about 10 µA to about 4 mA.

2. The method of claim 1, wherein three or four electrode shafts are used, and each electrode shaft has 1 to 3 platinum electrode bands.

3. The method of claim 1, wherein the defined infected area is treated sufficiently to destroy a bacterial infection or at least lessen the bacterial load within the defined infected area.

4. The method of claim 1, wherein the current vectors create a treatment zone within the defined infected area which is the summation of intersecting current vectors to induce an electrical DC voltage and low current or an ES zone which operates from electrolysis therapy.

5. The method of claim 1, wherein the defined infected area is within or around a bone of a patient.

6. The method of claim 1, wherein the infection is in tissue.

7. The method of claim 1, wherein the defined infected area is treated using 3 or more electrode shafts whereby the entire volume of bone or tissue within an electrical energy field defined by the electrodes is treated to systematically destroy or inactivate the infectious cells contained within the defined area, thereby reducing or eliminating the infection.

8. The method of claim 7, wherein reduction or elimination of the infection is accomplished using ES therapy with or without prescription drugs or surgery.

9. The method of claim 1, wherein the infection treated resulted from a leg bone fracture or a knee or hip replacement.

10. The method of claim 1, wherein the infection results from diabetes or another disease whereby antibiotics have failed to affect a cure of an infection but cannot cure the underlying disease condition.

11. The method of claim 1, wherein three or more electrodes are positioned substantially in a plane around the defined infected area and voltages applied to the electrodes are varied to steer current vectors dynamically and proportionally to and through the defined infected area.

* * * * *